US012761182B2

(12) United States Patent
Lim et al.

(10) Patent No.: US 12,761,182 B2
(45) Date of Patent: Oct. 13, 2026

(54) BIOSENSOR CARTRIDGES AND BIOSENSOR SYSTEM HAVING THE SAME

(71) Applicant: LG ELECTRONICS INC., Seoul (KR)

(72) Inventors: Kyoungtaek Lim, Seoul (KR); Taekyu Choi, Seoul (KR); Seonggeun Kim, Seoul (KR); Younghwan Kim, Seoul (KR); Changseok Kim, Seoul (KR); Kyungho Kong, Seoul (KR); Kyounghwa Kim, Seoul (KR); Youngrae Lee, Seoul (KR); Inkwan Yeo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 856 days.

(21) Appl. No.: 17/993,676

(22) Filed: Nov. 23, 2022

(65) Prior Publication Data

US 2023/0333100 A1 Oct. 19, 2023

(30) Foreign Application Priority Data

Apr. 19, 2022 (KR) ........................ 10-2022-0047913

(51) Int. Cl.
*G01N 27/414* (2006.01)
*A61B 5/05* (2021.01)
(Continued)

(52) U.S. Cl.
CPC ........... *G01N 27/4145* (2013.01); *A61B 5/05* (2013.01); *A61B 10/0045* (2013.01);
(Continued)

(58) Field of Classification Search
CPC ............. G01N 27/4145; G01N 27/414; G01N 33/48785; G01N 33/5438;
(Continued)

(56) References Cited

U.S. PATENT DOCUMENTS

| | | | |
|---|---|---|---|
| 9,805,165 | B2 | 10/2017 | Xiang et al. |
| 11,342,051 | B1 | 5/2022 | Jain et al. |

(Continued)

FOREIGN PATENT DOCUMENTS

| | | | |
|---|---|---|---|
| CA | 3175822 | A1 | 10/2021 |
| JP | 2000-258493 | A | 9/2000 |

(Continued)

OTHER PUBLICATIONS

Attached is the International Search Report for International Application No. PCT/KR2023/001417, dated May 15, 2023.

(Continued)

*Primary Examiner* — Samuel P Siefke
(74) *Attorney, Agent, or Firm* — Birch, Stewart, Kolasch & Birch, LLP

(57) ABSTRACT

A biosensor cartridge can include a circuit board including a connection terminal configured to be electrically connectable to an external diagnostic device, a sensor chip configured to detect a target material from an applied analysis specimen and transmit an electrical signal generated by reacting with the detected target material to the connection terminal of the circuit board, and a housing configured to accommodate the circuit board and the sensor chip and surround the circuit board and the sensor chip so that the connection terminal is exposed. The housing can include an accommodating portion that accommodates the analysis specimen.

15 Claims, 17 Drawing Sheets

(51) Int. Cl.

| | |
|---|---|
| ***A61B 10/00*** | (2006.01) |
| ***G01N 33/487*** | (2006.01) |
| ***G01N 33/543*** | (2006.01) |

(52) U.S. Cl.

CPC ..... *G01N 27/414* (2013.01); *G01N 33/48785* (2013.01); *G01N 33/5438* (2013.01); *B01L 2200/027* (2013.01); *B01L 2300/0636* (2013.01); *B01L 2300/0645* (2013.01); *B01L 2300/0663* (2013.01); *H01R 2201/20* (2013.01); *H05K 2201/10151* (2013.01)

(58) Field of Classification Search

CPC ....... G01N 33/48707; G01N 33/48771; G01N 33/48778; G01N 33/48792; G01N 27/4146; A61B 5/05; A61B 10/0045; A61B 5/0077; A61B 5/14546; A61B 5/1468; A61B 5/1486; A61B 5/4887; A61B 5/0002; A61B 5/061; A61B 2562/08; B01L 2200/027; B01L 2300/0636; B01L 2300/0645; B01L 2300/0663; B01L 3/502715; H01R 2201/20; H01R 13/465; H01R 13/6683; H01R 2201/12; H01R 12/72; H05K 2201/10151; H05K 2201/10265; H05K 1/181; H05K 2201/10166; H05K 2201/10386; G06K 7/1417; G06K 7/1447; G06Q 20/3223

See application file for complete search history.

(56) References Cited

U.S. PATENT DOCUMENTS

| | | | |
|---|---|---|---|
| 12,455,258 | B2 | 10/2025 | Kim et al. |
| 2004/0244151 | A1 | 12/2004 | Sakata et al. |
| 2008/0280285 | A1 | 11/2008 | Chen et al. |
| 2009/0124876 | A1 | 5/2009 | Nakamura et al. |
| 2014/0052475 | A1 | 2/2014 | Madan et al. |
| 2014/0273187 | A1 | 9/2014 | Johnson et al. |
| 2014/0308459 | A1 | 10/2014 | Miyazaki et al. |
| 2015/0083589 | A1 | 3/2015 | Lee et al. |
| 2015/0268186 | A1 | 9/2015 | Pagels |
| 2015/0352550 | A1 | 12/2015 | Bhargava et al. |
| 2016/0084793 | A1 | 3/2016 | Chen et al. |
| 2018/0272342 | A1 | 9/2018 | Samsoondar |
| 2019/0041355 | A1 | 2/2019 | Merriman et al. |
| 2019/0234907 | A1 | 8/2019 | Edwards et al. |
| 2020/0108385 | A1 | 4/2020 | Temiz et al. |
| 2020/0170552 | A1 | 6/2020 | Cho et al. |
| 2020/0333286 | A1 * | 10/2020 | Leon .................... H10D 62/149 |
| 2021/0003528 | A1 * | 1/2021 | Esquivel-Upshaw ........................ G01N 27/4146 |
| 2021/0129133 | A1 | 5/2021 | Ohta et al. |
| 2021/0285977 | A1 | 9/2021 | Tu et al. |
| 2021/0365445 | A1 | 11/2021 | Robell et al. |

FOREIGN PATENT DOCUMENTS

| | | | |
|---|---|---|---|
| JP | 2003-149192 | A | 5/2003 |
| JP | 2008-46094 | A | 2/2008 |
| JP | 2013-83506 | A | 5/2013 |
| JP | 2020-126077 | A | 8/2020 |
| KR | 20-0311804 | Y1 | 5/2003 |
| KR | 10-0813398 | B1 | 3/2008 |
| KR | 10-2008-0110356 | A | 12/2008 |
| KR | 10-2010-0072533 | A | 7/2010 |
| KR | 10-2010-0103932 | A | 9/2010 |
| KR | 10-2010-0136159 | A | 12/2010 |
| KR | 10-2011-0064754 | A | 6/2011 |
| KR | 10-2012-0101806 | A | 9/2012 |
| KR | 10-2013-0012744 | A | 2/2013 |
| KR | 10-1323373 | B1 | 10/2013 |
| KR | 10-2014-0120138 | A | 10/2014 |
| KR | 10-1507317 | B1 | 3/2015 |
| KR | 10-2016-0017684 | A | 2/2016 |
| KR | 10-1591379 | B1 | 2/2016 |
| KR | 10-2016-0065562 | A | 6/2016 |
| KR | 10-1779705 | B1 | 9/2017 |
| KR | 10-2030272 | B1 | 10/2019 |
| KR | 10-2019-0136580 | A | 12/2019 |
| KR | 10-2020-0144550 | A | 12/2020 |
| KR | 10-2021-0076854 | A | 6/2021 |
| KR | 10-2021-0151487 | A | 12/2021 |
| WO | WO 2019/208901 | A1 | 10/2019 |
| WO | WO 2021/013392 | A1 | 1/2021 |
| WO | WO 2021/224907 | A1 | 11/2021 |

OTHER PUBLICATIONS

Also attached is the International Search Report for International Application No. PCT/KR2023/001423, dated May 24, 2023.

Also attached is the International Search Report for International Application No. PCT/KR2023/002760, dated Jun. 20, 2023.

Also attached is the International Search Report for International Application No. PCT/KR2023/002762, dated Jun. 20, 2023.

Also attached is the International Search Report for International Application No. PCT/KR2023/002765, dated Jun. 20, 2023.

Cheah et al., "Integrated Platform Addressing the Finger-Prick Blood Processing Challenges of Point-of-Care Electrical Biomarker Testing", Analytical Chemistry, vol. 94, No. 1, published Jan. 3, 2022, pp. 1256-1263.

Tran et al., "Toward Intraoperative Detection of Disseminated Tumor Cells in Lymph Nodes with Silicon Nanowire Field Effect Transistors", ACS Nano, vol. 10, No. 2, published on Feb. 9, 2016, pp. 2357-2364.

Sommers et al., "Self-propelled water droplet movement on a laser-etched radial gradient copper surface," Applied Thermal Engineering, vol. 173, No. 115226, 2020, pp. 1-12.

* cited by examiner

BIOSENSOR CARTRIDGES AND BIOSENSOR SYSTEM HAVING THE SAME

CROSS-REFERENCE TO RELATED APPLICATIONS

This application claims priority to the Korean Patent Application No. 10-2022-0047913 filed in the Republic of Korea on Apr. 19, 2022, which is hereby incorporated by reference in its entirety into the present application.

BACKGROUND

Field

The present disclosure relates to a biosensor cartridge including a biosensor and a biosensor system including the biosensor cartridge.

Discussion of the Related Art

Recently, as diseases having a high infectivity spread, a need for rapid diagnosis and self-diagnosis of the disease in medical fields such as homes, hospitals, and public health centers is increasing.

Therefore, it is required to develop an immunoassay platform that does not require specialized knowledge or complicated procedures and has a short analysis time.

A biosensor generates an electrical, optical signal, and a color that changes according to a selective reaction between probe material having reactivity for a specific target material contained in a body fluid such as sweat and saliva, or in biological substances such as blood or urine, and the target material. Accordingly, the presence of a specific target material can be checked by using the biosensor.

Conventionally, a strip-type rapid kit has been widely used, and simple color development (e.g., the test, such as a dipstick, will change colors if the results are positive) is performed by determining whether a bio-target material having a certain concentration or higher is present.

However, in the case of labeling the target material by color development, the conversion of color development can be inaccurate depending on the concentration of the target material, and the color development must be visually determined. Therefore, the accuracy is different depending on a user who views the test results.

To compensate for this inaccuracy, a biosensor that generates an electrical signal, as opposed to a color development, has been proposed.

In a biosensor that generates an electrical signal, a target material is coupled to a small thin film semiconductor structure, an electrical conductivity of the semiconductor structure is changed by the target material, and the target material is detected through a change in electrical conductivity. In particular, when a target material is combined (e.g., disposed) in a channel, if an electrochemical reaction occurs or the target material itself has a charge, electrons or holes in the semiconductor structure are accumulated or depleted due to the electric field effect caused by the combination of the probe material and the target material. Thus, the electrical conductivity is changed, which is read as a change in the amount of current. In such an electrochemical-based biosensor, the resistance of an electrode itself and the interfacial property of a channel where the electrochemical reaction occurs can be rather important.

On the other hand, a biosensor having channels in the semiconductor structure has a very thin thickness since the electrodes for measuring an electrical signal are also manufactured in a dicing unit (e.g., a process where a sheet of electrodes is diced or cut into individual electrodes, which can be performed using a laser, for instance). Thus, a short circuit or contamination can occur due to damage to an electrode or a channel while the biosensor is coupled to a measurement device for measuring the amount of current.

To prevent the damage (e.g., from a short circuit), a conventional biosensor is configured to have a structure including a sensor unit for sensing a target material and a connection portion for connecting the sensor unit to a measurement device.

In other words, the electrode of the conventional biosensor can be configured to have a connection portion extending from the sensor unit for sensing a target material and expanding at the end of a substrate to be connected to the measurement device.

However, even if an electrode is formed from expansion as described above, since the electrode is formed in a dicing step, the size of the sensor chip itself can increase, which unnecessarily increases the semiconductor wafer, and can lower the chip yield.

In addition, when the conventional biosensor senses a signal from the electrode while in direct contact with a measurement device, an external force is directly applied to the biosensor chip, which can cause cracks therein.

To prevent a crack from being generated, a process of performing wire bonding has been started, which separately provides a sensor chip and a circuit board and connects them electrically.

However, since the wire bonding is performed after attachment of a reactant to the biosensor chip, namely, after activation in the biosensor chip, and soldering is performed at a very high temperature, a bio-reactive material composed of a protein vulnerable to heat can be denatured.

Protein denaturation can degrade the reactivity of the biosensor chip itself and reduces its reliability.

In addition, the entire sensor chip has to be discarded if a defect in the sensor chip is found from inspection after wire bonding of the sensor chip and the circuit board; accordingly, an increase in the defect rate causes a higher manufacturing cost.

In the case of a biosensor chip using a test specimen composed of liquid to induce a reaction with the sensor chip, when the test specimen flows into an area other than the reaction area of the sensor chip, a short circuit can occur as the test specimen comes into contact with other parts of the electrode.

Also, in the related art, a dedicated measurement device was used to measure the signal of the biosensor.

A dedicated measurement device for biosensors is huge and requires expensive precision measurement equipment. Because a measurement process is performed manually, the dedicated measurement device exhibits poor reproducibility, takes a long diagnosis time, and requires costly equipment to build a whole system.

When it is necessary to periodically measure concentration, such as blood sugar, diabetes, or blood pressure, or to observe disease recurrence after treatment periodically, high-sensitivity measurement of a bio-material present in small amounts in body fluids is required, and whenever a new disease comes to the fore, system development is required for a cure of the new disease, making it difficult to use a dedicated measurement device for general purposes.

For this purpose, a simplified measurement device has been proposed. However, in the case of a simplified measurement device, while being coupled to a sensor, the measurement device contacts a bio-target material for detection, resulting in contamination of the measurement device and causing a reliability problem for the measurement accuracy when the sensor is replaced.

Private hospitals or homes are unable to afford such a dedicated measurement device to perform analysis of a biosensor, and a simplified measurement device suffers a reliability problem, making it difficult to be actively utilized.

ART REFERENCES

Korean Patent Application Publication No. 2010-0136159 (Date: Dec. 28, 2010)

Korean Patent Application Publication No. 2020-0144550 (Date: Dec. 29, 2020)

SUMMARY OF THE DISCLOSURE

The present disclosure has been made in view of the above limitations and can provide a biosensor cartridge including a sensor chip to minimize an effect on the sensor chip when being coupled to a diagnostic device.

The present disclosure further provides a biosensor chip, a biosensor cartridge including a circuit board connected to the biosensor chip, and a connecting member capable of implementing both physical connection and electrical connection between the biosensor chip and the circuit board to prevent degradation of the sensor chip.

The present disclosure further provides a sensor cartridge shape capable of optimizing the shape of a housing protecting a biosensor chip and a circuit board to prevent a test specimen from leaking into the circuit board.

The present disclosure further provides a cartridge structure for reinforcing rigidity of a connection terminal coupling a cartridge and a diagnostic device.

A biosensor cartridge according to the present disclosure comprises a circuit board including a connection terminal configured to be electrically connectable to an external diagnostic device; a sensor chip configured to detect a target material from an applied analysis specimen and transmit an electrical signal generated by reacting with the detected target material to the connection terminal of the circuit board; and a housing configured to accommodate the circuit board and the sensor chip and surround the circuit board and the sensor chip so that the connection terminal is exposed, wherein an accommodating portion that accommodates the analysis specimen and opens the sensor chip's sensor area in which a reactant reacting specifically with the target material is disposed is formed on one surface of the housing.

The connection terminal is formed by protruding from one side surface of the housing and includes at least three pins disposed in parallel on the circuit board by being separated from each other.

The sensor chip further includes a pad area that transmits an electrical signal transmitted from the sensor area to the circuit board, wherein the sensor area includes a board; a channel area forming at least one of the channels on the board; a source electrode and a drain electrode that overlap with both ends of each of the channels and are formed to be spaced apart from each other; a gate electrode that is spaced apart from the source electrode and the drain electrode and applies a bias voltage to the analysis specimen; and a passivation layer that covers the entire sensor chip and opens only an upper portion of the channel area and the gate electrode, wherein a source pad, a drain pad, and a gate pad connected respectively to the source electrode, the drain electrode, and the gate electrode of the sensor area can be formed in the pad area.

The circuit board can include a board opening that opens the sensor area of the sensor chip, and a plurality of connection pads corresponding to the pad areas of the sensor chip can be formed around the board opening.

Each of the plurality of connection pads is connected one-to-one to each of the source pad, the drain pad, and the gate pad of the sensor chip, and the biosensor cartridge can further include a plurality of connecting members performing one-to-one connection of connection pads of the circuit board to the source pad, the drain pad, and the gate pad of the sensor chip.

The housing includes a lower housing and an upper housing that faces the lower housing and forms a space accommodating the sensor chip and the circuit board therein; the sensor chip is disposed on the inner surface of the lower housing, and the circuit board is disposed on the sensor chip so that the sensor area of the sensor chip is opened and the pad area of the sensor chip comes into contact with a connection pad of the circuit board; and the plurality of connecting members are attached between the pad area of the sensor chip and the connection pad of the circuit board.

The plurality of connecting members can include a first surface in contact with a connection pad of the circuit board and a second surface bent from the first surface and in contact with a pad area of the circuit chip and conduct electricity between the circuit board and the sensor chip through elastic contact due to assembling of the housing.

The upper housing and the lower housing can be fused and integrated while accommodating the sensor chip and the circuit board.

The circuit board can include a first surface on which the connection terminal is formed and can further include a reinforcing member that entirely covers a second surface opposing the first surface.

The accommodating portion of the housing is recessed from the upper surface, has an inclined surface, the diameter of which is gradually decreased away from the upper surface, and accommodates the specimen from the outside with the sensor area of the inner sensor chip being open, and further includes a sealing part sealing between the end of the inclined surface and the sensor area.

The sealing part can include a sealing opening having a larger diameter than the diameter of the end of the inclined surface and can be aligned with the accommodating portion and the sensor chip so that the sealing opening exposes the sensor area.

A rear surface of the inclined surface of the accommodating portion can further include a step portion coupled to an end surface of the board opening in an area in contact with the board opening of the circuit board.

The sealing part can be formed of a material different from that of the upper housing and sequentially molded, injected, and cured to be integrated with the upper housing.

The accommodating portion can further include a guide wall protruding upward from the upper surface of the housing and accommodating the specimen.

The accommodating portion can further include a guide groove that is recessed to surround the guide wall on the upper surface of the housing and accommodate the specimen flowing from the guide wall.

On the other hand, the present disclosure provides a biosensor system comprising a biosensor cartridge, one side of which exposes a connection terminal that outputs an electrical detection signal generated according to target material within an applied specimen; and an integrated diagnostic device including an insertion hole on the front surface through which the connection terminal of the biosensor cartridge is inserted, analyzing the detection signal from the biosensor cartridge through the insertion hole, diagnosing the existence of the target material, and displaying the diagnosis result on a display area; wherein the biosensor cartridge includes a sensor chip including a sensor area reacting with the target material, a circuit board connected to the sensor chip and forming the connection terminal at one end thereof, and a housing that covers to accommodate the circuit board and the sensor chip therein and exposes the connection terminal to one side surface.

An accommodating portion that accommodates the specimen and opens the sensor area of the sensor chip is formed on the upper surface of the housing, and the connection terminal is formed at one end of a circuit board protruding from one side surface of the housing and includes at least three pins disposed in parallel by being separated from each other.

The accommodating portion can be formed on the upper surface of the housing, and the connection terminal can be formed at one end of the upper surface of the circuit board.

The connection terminal can be formed of a SD card chip type, USB-A type or a USB-C type.

Through the solution above, the present disclosure provides a biosensor cartridge coupled to a diagnostic device through a terminal of a circuit board connected to a sensor chip, thereby minimizing the effect on the sensor chip when being coupled to a diagnostic device.

In addition, the present disclosure provides a biosensor cartridge including a biosensor chip and a circuit board connected thereto and applies a connecting member that simultaneously implements physical and electrical coupling between the biosensor chip and the circuit board without soldering, thereby preventing degrading of the sensor chip, dramatically reducing the defect rate of the sensor chip, and improving the reliability of the sensor cartridge.

In addition, the present disclosure optimizes the shape of a housing protecting a biosensor chip and a circuit board to prevent a test specimen from leaking into the circuit board, thereby preventing the circuit board form being short-circuited.

Also, the present disclosure reinforces the rigidity of a connection terminal performing coupling between a cartridge and a diagnostic device, thereby protecting the circuit board when being inserted into the diagnostic device.

DETAILED DESCRIPTION OF THE EMBODIMENTS

Figure 1:
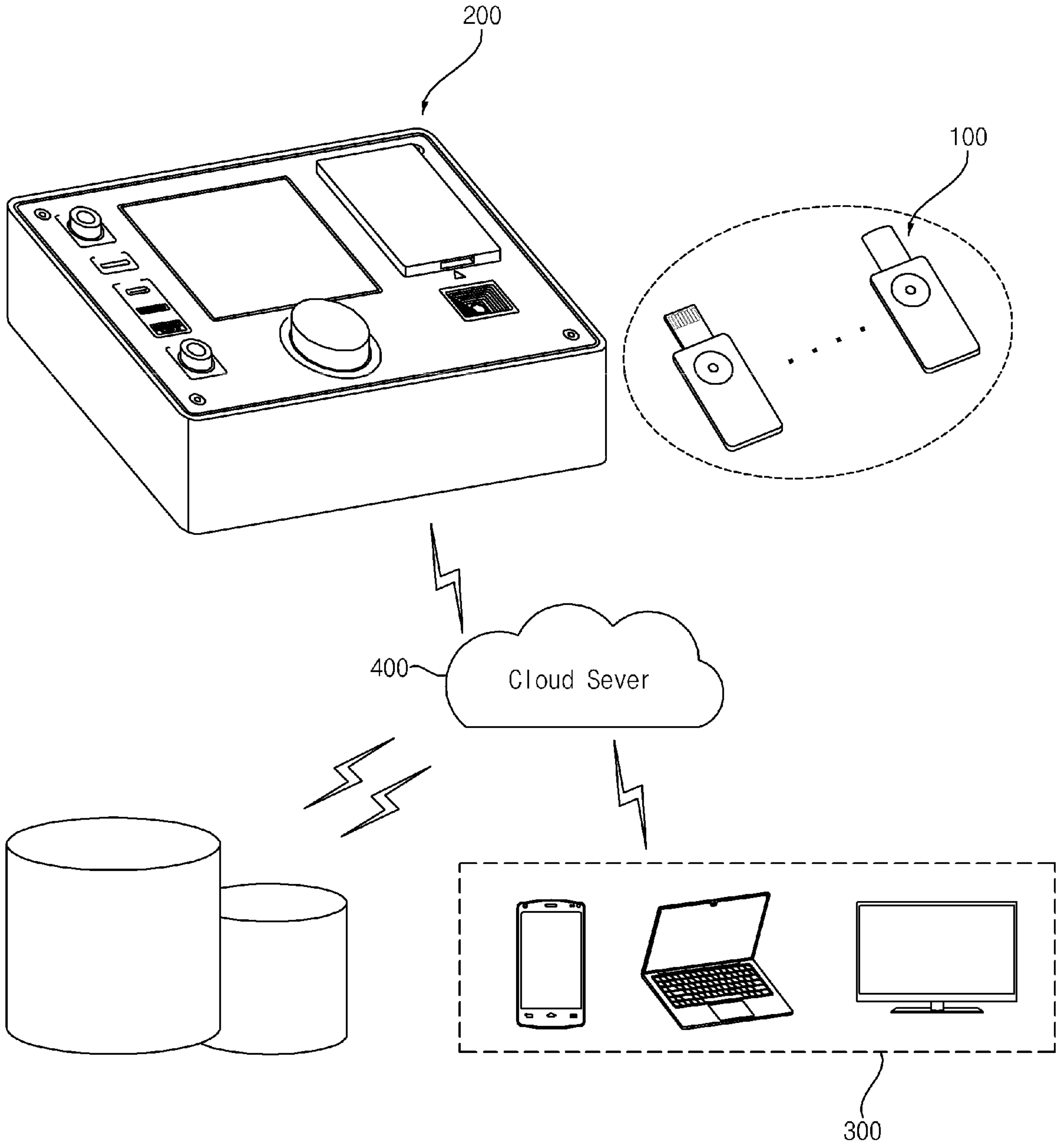
FIG. 1 is a diagram illustrating a biosensor system according to one or more embodiments of the disclosure.

Expressions referring to directions such as "front(F)/rear (R)/left (Le)/right (Ri)/up (U)/down (D)" mentioned below are defined as shown in the drawings, but this is for the purpose of explaining an embodiment so that it can be clearly understood, and it is obvious that each direction can be defined differently depending on where standard is set.

The use of terms such as 'first, second', etc. added before the components mentioned below is only to avoid confusion of the referred components, and is irrelevant to the order, importance, or master-slave relationship between the components. For example, an embodiment including only a second component without a first component can also be implemented.

In the drawings, the thickness or size of each component is exaggerated, omitted, or schematically illustrated for convenience and clarity of description. In addition, the size and area of each component do not fully reflect the actual size or area.

In addition, angles and directions mentioned in the process of explaining a structure of the present embodiment are based on those described in the drawings. In the description of the structure in the specification, if a reference point for the angle and a positional relationship are not clearly mentioned, the related drawings can be referred to.

In the present specification, target materials are biomaterials representing a specific substrate, and are interpreted as having the same meaning as analytical bodies or analytes. In the present embodiment, the target material can be an antigen. In the present specification, probe material is a biomaterial that specifically binds to a target material and is interpreted as having the same meaning as a receptor or an acceptor. In the present embodiment, the probe material can be an antibody.

The electrochemical-based biosensor combines the analytical ability of the electrochemical method with a specificity of biological recognition and detects a biological recognition phenomenon for a target material as a change in current or potential, by immobilizing or containing a material having biological specificity, i.e., probe material such as an enzyme, an antigen, an antibody, or a biochemical material, on the surface of an electrode.

Hereinafter, a biosensor system according to the present embodiment will be described with reference to FIGS. 1 and 2.

Figure 2:
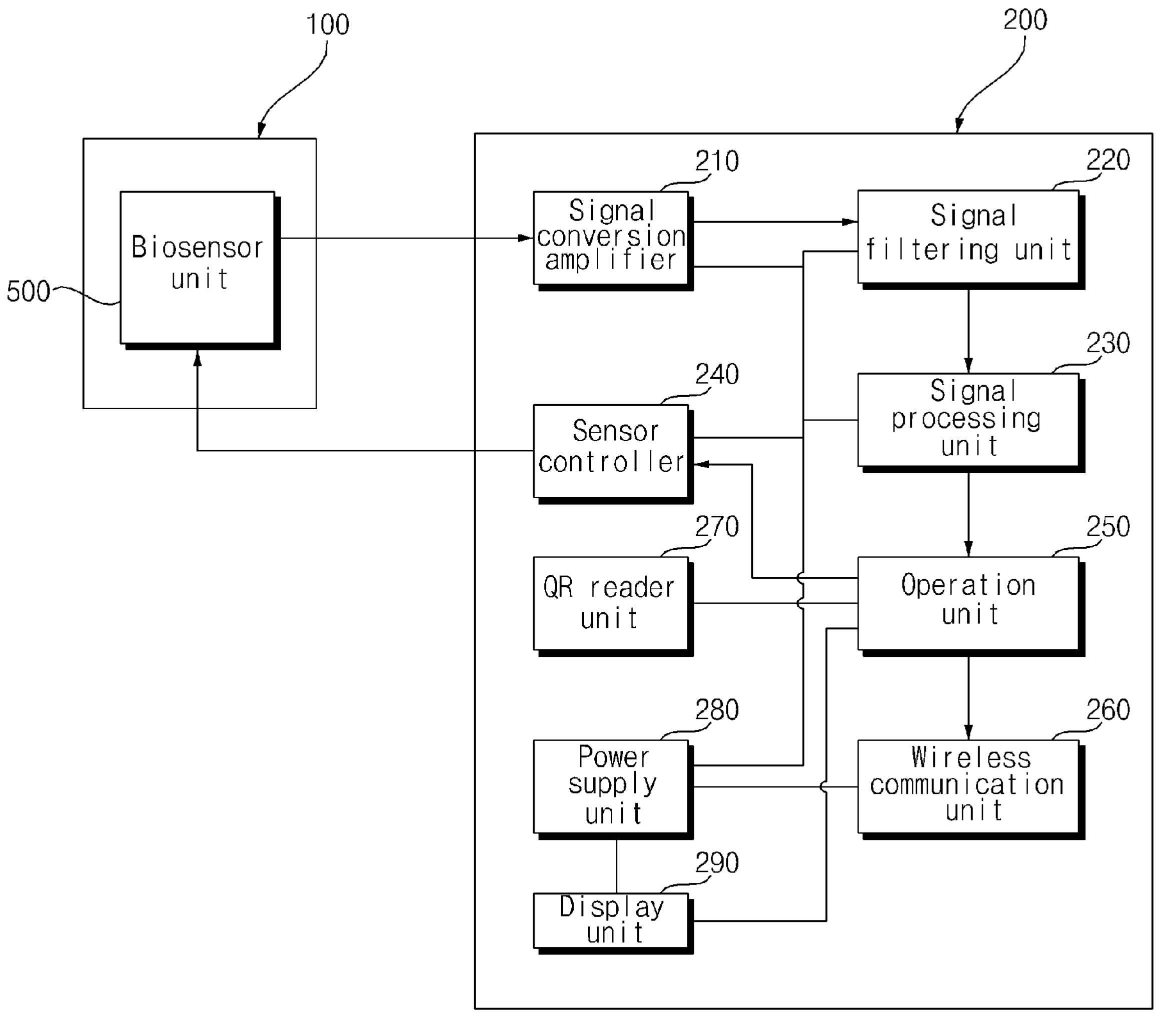
FIG. 2 is a configuration diagram of a biosensor diagnostic device and a biosensor cartridge of FIG. 1.

FIG. 1 is a diagram illustrating a biosensor system according to the present embodiment, and FIG. 2 is a configuration diagram of a biosensor diagnostic device 200 and a biosensor cartridge 100 of FIG. 1.

Referring to FIG. 1, the biosensor system according to the present embodiment includes a biosensor diagnostic device 200, a plurality of biosensor cartridges 100, and at least one server 400.

When the plurality of biosensor cartridges 100 are inserted (e.g., the plurality of biosensor cartridges 100 can be inserted into the biosensor diagnostic device 200 simultaneously), the biosensor diagnostic device 200 reads a detection signal from the biosensor cartridge 100 to read the presence of a target material for each biosensor cartridge 100.

The biosensor diagnostic device 200 is a portable integrated diagnostic device 200 that detects a current change for the presence of a trace amount of a target material from the biosensor cartridge 100, and accordingly diagnoses a disease and delivers the diagnosis result to a user.

To this end, the biosensor diagnostic device 200 can be provided to be portable by integrating each functional block, miniaturizing it, and integrating it in one case.

The biosensor diagnostic device 200 can be moved regardless of location, regardless of the presence or absence of an external power source by mounting a battery 281 therein. In addition, the diagnostic device 200 includes a function of compensating a reproducibility and non-uniformity of a sensor by including a pre-processing process of correcting a detection signal from the biosensor cartridge 100 so as to be able to read a minute signal change.

In addition, the biosensor diagnostic device 200 includes a QR reader that reads a QR code disposed on the rear surface of the biosensor cartridge 100 and receives environmental information for genuine product certification of the biosensor cartridge 100 to perform genuine product certification and a communication module that can transmit and receive signals for genuine product certification with an external cloud server 400.

In the biosensor diagnostic device 200, a program algorithm or application for diagnosing a disease by measuring and analyzing the detection signal from the biosensor cartridge 100 can be installed, and different algorithms are executable according to the type of each biosensor cartridge 100. That is, each type of biosensor cartridge 100 will require a different algorithm or application, the different algorithms/applications are stored a memory of the biosensor diagnostic device 200.

In addition, the biosensor diagnostic device 200 includes a display unit 290 for directly displaying the diagnosis result to a user and is designed to be directly manipulated through a user interface 296, 297, 294.

The detailed configuration of the integrated biosensor diagnostic device 200 will be described later.

Meanwhile, the biosensor system includes a plurality of biosensor cartridges 100 which is inserted into the biosensor diagnostic device 200 to provide detection signals.

Each of the biosensor cartridges 100 is electrically connected to a diagnostic device 200 in which an algorithm capable of measuring and analyzing an electrical detection signal generated in a biosensor chip 500 is installed.

Specifically, as shown in FIG. 1, the biosensor cartridge 100 can be inserted into and electrically connected to a cartridge insertion module 2911 of the integrated biosensor diagnostic device 200.

The biosensor cartridge 100 can accommodate the sensor chip 500 corresponding to a biosensor unit 500 (e.g., the sensor chip 500 can be designated a biosensor unit 500) in a housing 110, 120, and the housing 110, 120 can accommodate a circuit board 150 including a circuit pattern that extends to a connection terminal 153 that is connected to an electrode pad of the sensor chip 500 and inserted into the insertion module 2911 of an external biosensor diagnostic device 200.

The housing 110, 120 can be separated into an upper housing 110 and a lower housing 120, and the upper housing 110 and the lower housing 120 are coupled and fixed to each other while accommodating the sensor chip 500 and the circuit board, thereby constituting a single biosensor cartridge 100.

The biosensor cartridge 100 has a connection terminal 153 for physical and electrical coupling with the biosensor diagnostic device 200 exposed from one end to the outside, and a solution accommodating portion 119 for accommodating a specimen (e.g., analysis specimen) is formed on the surface (e.g., an upper surface) of the upper housing 110.

The solution accommodating portion 119 exposes a part of the inner sensor chip 500, and when a specimen is accommodated in the solution accommodating portion 119, the charge concentration of a channel of the sensor chip 500 is varied according to the antigen-antibody reaction of the sensor chip 500, so that the current flowing through the electrode of the sensor chip 500 varies. The varied current is read by the diagnostic device 200 through the connection terminal 153.

In this case, in order to secure the charge mobility of the sensor chip 500, a channel can be implemented with various materials, and in particular, a channel can be implemented by using graphene. However, alternate materials can be used for the channel of the sensor chip 500, such as silicon, silicon carbide, germanium, aluminum nitride, indium, gallium nitride and gallium arsenide.

The detailed configuration of the biosensor cartridge 100 will be described in detail later.

Meanwhile, the biosensor system can include at least one server 400.

The server 400 can be a manufacturer server 400, and the server 400 can include a processor capable of processing a program. The function of the server 400 can be performed by the manufacturer's central computer (e.g., a cloud computer).

For example, the server 400 can be a server 400 operated by a manufacturer of the biosensor cartridge 100 and the diagnostic device 200. As another example, the server 400 can be a server 400 that is provided in a building, and stores state information on devices in the building or stores content required by home appliances in the building.

The server 400 can store firmware information and diagnostic information on the diagnostic device 200 and transmit certification information on the biosensor cartridge 100 requested from the diagnostic device 200.

The server 400 in a biosensor system can be one of a plurality of cloud servers 400 of a manufacturer and can be provided within the biosensor system while a plurality of cloud servers 400 are simultaneously included to allow access to one biosensor diagnostic device 200.

As described above, when a plurality of cloud servers 400 can simultaneously access one biosensor diagnostic device 200, the biosensor diagnostic device 200 can match the ranks with respect to the plurality of cloud servers 400 and can send a certification request sequentially from the highest priority. In this case, if a response signal is not received from the priority server 400, a certification request can be sent to the server 400 of the next priority.

The server 400 can authenticate the biosensor cartridge 100 and provide the certification result to the biosensor diagnostic device 200.

In addition, the server 400 can provide calibration data and update data for the product of a corresponding ID and can transmit to the communicating biosensor diagnostic device 200.

The server 400 can also generate and distribute an upgraded version of a program for analysis for each biosensor cartridge 100.

To this end, the server 400 can receive history information on the manufacturing date, manufacturing conditions, sensor type, test result, etc. of the biosensor cartridge 100 of a manufacturer from a manufacturing server of a separate manufacturer.

In addition, the server 400 can periodically generate and distribute an upgraded version of a program provided to each diagnostic device 200 by receiving, accumulating, and machine learning the diagnostic result values for a corresponding product.

Meanwhile, the biosensor system of the present embodiment can further include a plurality of user terminals 300 but is not limited thereto.

When the user terminal 300 is included in the system, the biosensor diagnostic device 200 or the cloud server 400 can transmit data on the diagnosis result to the communicating user terminal 300.

To this end, a dedicated application for the user terminal 300 can be provided from the manufacturer server 400, and various processing of diagnostic data is possible by storing and executing the application in the user terminal 300.

For example, when a user is infected with the same disease for a long period of time, data processing is possible so that periodic test results can be accumulated and displayed, and the processed results can be provided to the user terminal 300 through an application. Accordingly, the user terminal 300 can be able to determine the prognosis for the disease and the expected treatment time.

The user terminal 300 can be, for example, a laptop, a smart phone, a tablet, or the like on which an application is installed.

The user terminal 300 can communicate (e.g., via wired or wireless communication) directly with the diagnostic device 200 or the server 400 through a network, and the diagnostic device 200 and the server 400 can also communicate directly through a network.

In this case, wireless communication technologies such as, IEEE 802.11 WLAN, IEEE 802.15 WPAN, UWB, Wi-Fi, Zigbee, Z-wave, and Blue-Tooth can be applied to the network and can include a wireless communication unit 260 of each device (the user terminal 300 and the diagnostic device 200) to apply at least one or more communication technologies.

The wireless communication unit 260 can be changed depending on the communication method of other devices (the user terminal 300 and the diagnostic device 200) or the server 400 that is a target to communicate with.

As described above, in the biosensor system, the connection terminal 153 of the biosensor cartridge 100 accommodating the specimen is inserted into and electrically connected to the portable integrated biosensor diagnostic device 200 so that a detection signal is read.

The functional configuration of the biosensor diagnostic device 200 for reading the detection signal is shown in FIG. 2.

Referring to FIG. 2, the biosensor diagnostic device 200 includes a plurality of function modules.

Each functional module can be individually packaged and accommodated in the case of one biosensor diagnostic device 200, and a plurality of functional modules can be packaged as one module and accommodated in a case 201, 202.

The biosensor diagnostic device 200 includes a signal conversion amplifier 210, a signal filtering unit 220, a signal processing unit 230, an operation unit 250, a wireless communication unit 260, a power supply unit 280, a display unit 290, a QR reader unit 270, and a sensor controller 240.

The signal conversion amplifier 210 receives firstly a detection signal transmitted from the biosensor cartridge 100 and converts and amplifies the current value of the detection signal so that the current value can be read by the biosensor diagnostic device 200.

The signal conversion amplifier 210 can have an analog circuit including a resistor that generates a voltage drop according to a changed current value which is a detection signal transmitted from the biosensor cartridge 100 and can further include an amplifying circuit that receives and amplifies such a voltage drop.

The amplified signal is transmitted to the signal filtering unit 220 to remove noise and then transmitted to the signal processing unit 230. The signal processing unit 230 can convert the amplified analog sensing value from which the noise has been removed into a digital value for a diagnostic operation and can include an analog-digital converter (ADC) for this purpose.

As described above, the signal conversion amplifier 210, the signal filtering unit 220, and the signal processing unit 230 can all be implemented as a single integrated circuit chip. Such an integrated circuit chip can correspond to a cartridge insertion module 211 in FIG. 3.

The sensor controller 240 can provide a reference voltage whose level is changed according to the control of the operation unit 250 to the connection terminal 153 of the connected biosensor cartridge 100, and the biosensor cartridge 100 receives a reference voltage having a varied level from the sensor controller 240 and flows a current value changed by a varied resistance value of channel to the connection terminal 153. The connection terminal can be disposed at one side of the biosensor cartridge 100. The sensor controller 240 can be mounted together as a voltage level conversion circuit in the integrated circuit chip.

Meanwhile, the biosensor diagnostic device 200 includes an operation unit 250 for controlling the operation of the diagnostic device 200 and reading a received digitized detection value.

The control of the diagnostic device 200 can include a separate controller (e.g., hardware-embedded processor), but it is possible to simultaneously read whether a detection value is detected and control the operation of the entire diagnostic device by executing a program stored in one controller.

In this case, the operation unit 250 can be implemented as a separate integrated circuit chip and can be mounted in a main board 255.

The operation unit 250 can read whether there exists a target material for the detection value according to the reading program, process the result and provide the result to the display unit 290. In addition, such a reading result can be transmitted to a cloud server 400 and a user terminal 300 through a wireless communication unit 260.

The operation unit 250 can also control the operation of the diagnostic device 200 for the reading. For example, when the connection terminal 153 of the biosensor cartridge 100 is inserted into the cartridge insertion module 211, the operation unit 250 can detect the insertion and transmit a QR reading command to the QR reader unit 270.

Accordingly, the QR reader unit 270 performs an operation for reading the QR code attached to the rear surface of the biosensor cartridge 100 inserted into the cartridge insertion module 211 and transmits the information back to the operation unit 250.

The operation unit 250 receives the QR information, performs a certification request to the cloud server 400 accordingly, and when certification information is received from the cloud server 400 and confirmed as genuine, performs reading for the biosensor cartridge 100, and matches the reading result with the certification result of the biosensor cartridge 100 and processes it.

Accordingly, the operation unit 250 can reduce the error by minimizing the time difference of the result matching (e.g., minimizing the time to determine if the biosensor cartridge 100 is genuine) by simultaneously executing the module control of the diagnostic device 200 and the execution of the read program.

The operation unit 250 can include a memory card (e.g., flash memory) as a data storage unit, a library file for diagnosing biomaterials, and an embedded system board equipped with a signal processing device. For example, a memory card capable of storing output signal data is inserted into the embedded system board, and a system operating system (OS), driving program, library file for analysis, and the like are stored in the memory card. In addition, signal processing for concentration analysis of biomaterials is calculated through comparison analysis with library files in the central processing unit (CPU) of the embedded system board, and the analyzed result is stored again in the memory card. In addition, the wireless communication unit 260 can be mounted together in such an embedded system board but is not limited thereto.

The biosensor diagnostic device 200 includes a display unit 290 as a user interface, and the display unit 290 includes a liquid crystal display device, an OLED or LED display device, a touch panel, and the like to display an analyzed result detected by creating a program considering a user's convenience. As a user interface, it can include various types of terminals, dials, buttons, and the like.

A terminal 297, a dial 296, a button 294, and the like turn on/off the operation of the biosensor diagnostic device 200 and can be connected to the operation unit 250 to control the operation unit 250 according to a user command. That is, as a user's command is input in the interface 297, 296, 294, the diagnosis of the biosensor cartridge 100 can be started. The display unit 290 displays the progress process during the diagnosis process and displays the diagnosis result after the completion of diagnosis.

The biosensor diagnostic device 200 includes a separate power supply unit 280 capable of applying power to a plurality of modules, and the power supply unit 280 includes a battery 281. Accordingly, it is possible to supply power to the internal module from the battery 281, and thus the device 200 can be portable. The battery 281 can be charged by an external power source, such as alternating current AC power available from the utility.

Hereinafter, a detailed structure according to an example of the biosensor diagnostic device 200 will be described with reference to FIGS. 3 and 4.

Figure 3:
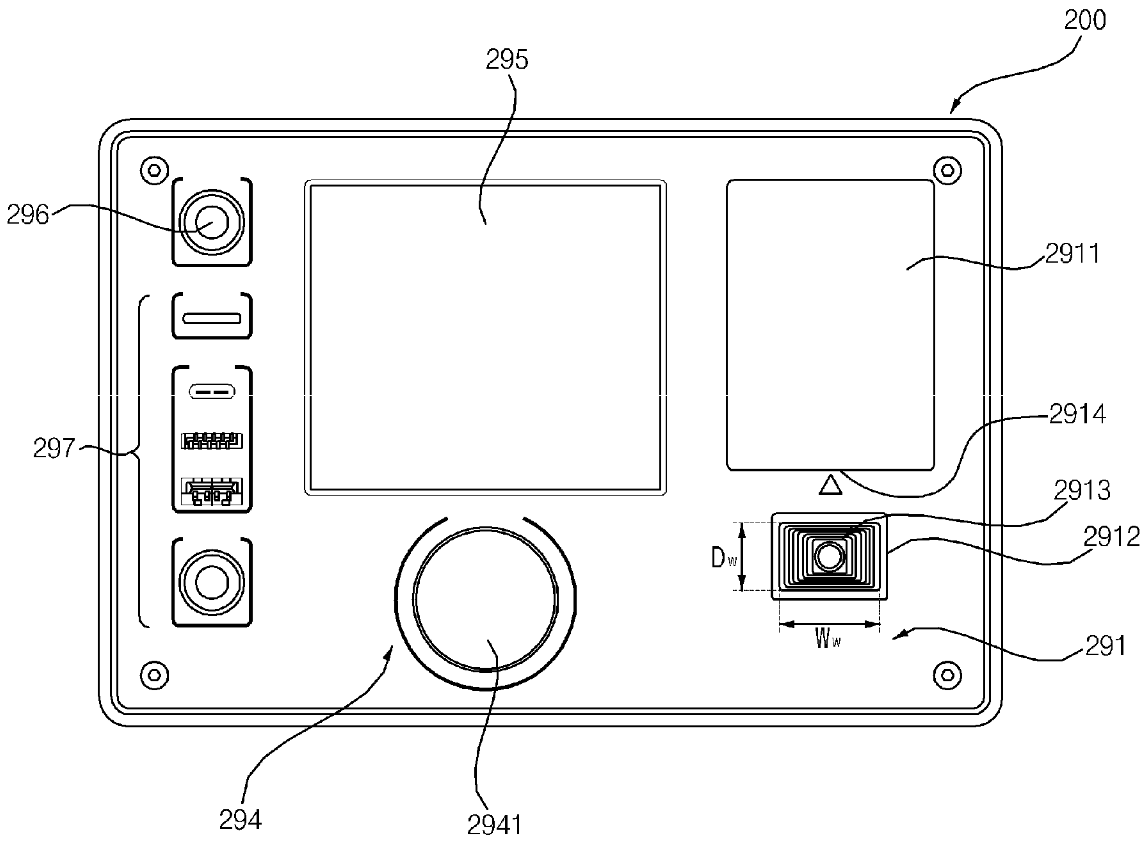
FIG. 3 is a front view of an example of the biosensor diagnostic device of FIG. 1.
Figure 4:
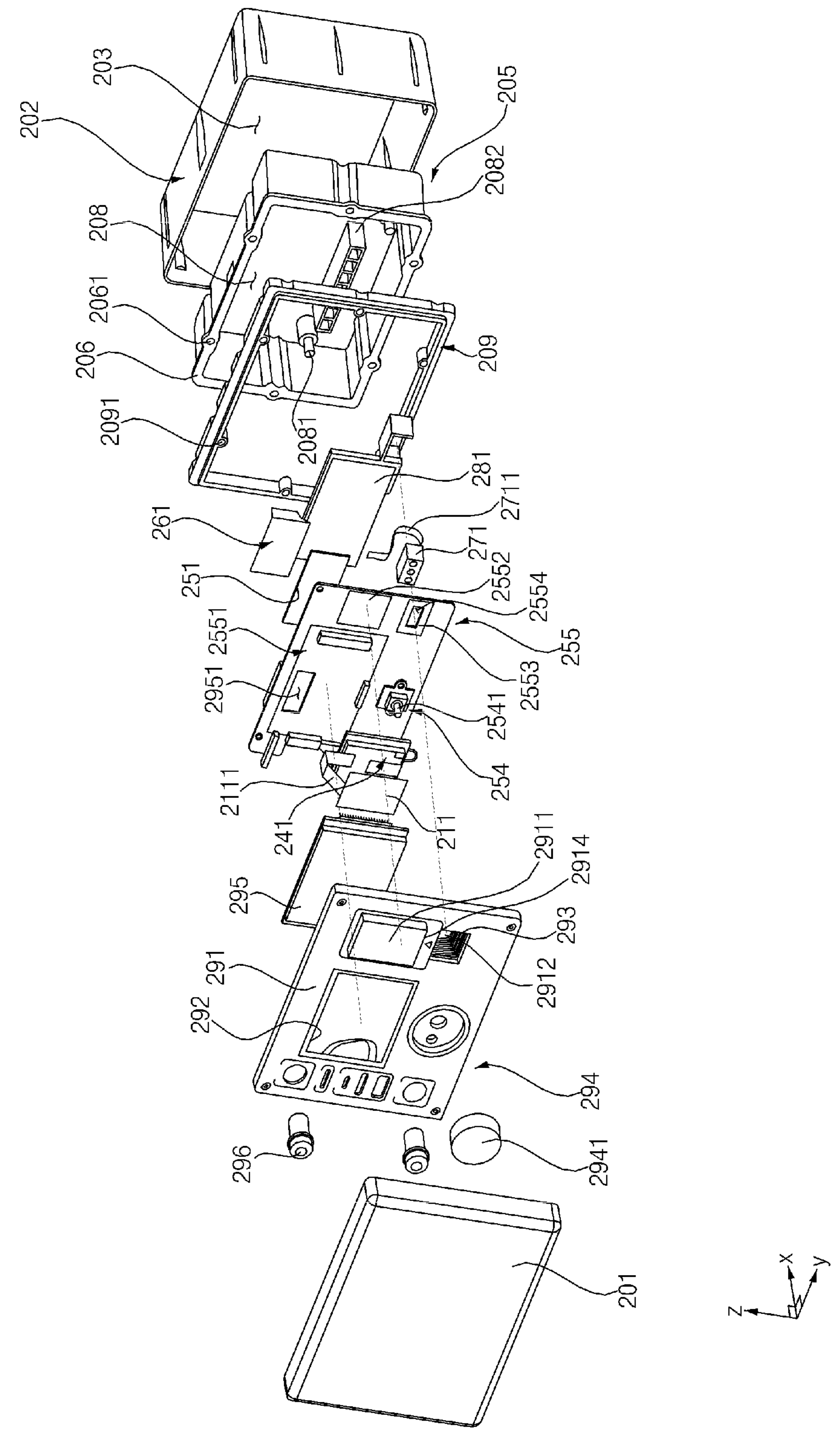
FIG. 4 is an exploded perspective view of the biosensor diagnostic device of FIG. 3.

FIG. 3 is a front view of an example of the biosensor diagnostic device 200 of FIG. 1, and FIG. 4 is an exploded perspective view of the biosensor diagnostic device 200 of FIG. 3.

Referring to FIGS. 3 and 4, the biosensor diagnostic device 200 according to the present embodiment is provided as a portable integrated device.

Here, the state of being integrated can include all states recognized as a single device in movement, disposition, and use of the diagnostic device 200. For example, the state of being integrated can mean that that it is located together inside the same case and is integrated by the same case, can mean that it is fixed by being fitted or attached to the same member and integrated by the same member, can mean that it is formed together in the same member to constitute a part of the same member, or can mean that it is wrapped or fixed together by the same member. On the other hand, it can be difficult to be considered as being integrated in the case of being connected by a separate output cable or the like.

The integrated biosensor diagnostic device 200 according to the present embodiment can include a separate inner cover 205 inside the case 201, 202. A front panel 291 is disposed to cover a plurality of modules accommodated in an accommodating portion 208 of the inner cover 205 and a front surface of the inner cover 205. In this case, one of a rear case 202 and the inner cover 205 can be omitted.

In the exploded perspective view of FIG. 4, the left side is defined as a front surface and the right side is defined as a rear surface along the X axis where the plurality of modules overlap, and the Y axis and Z axis perpendicular to the X axis are defined as two axes that forms a reference plane of the front panel 291 provided to a user.

The case 201, 202 of the biosensor diagnostic device 200 according to the present embodiment can include a front case 201 and a rear case 202. The rear case 202 is formed to have an accommodating portion 203 therein, and to have a bottom surface and a side surface. The accommodating portion 203 accommodates at least the inner cover 205, the main board 255 and the front panel 291. However, the accommodating portion 203 can accommodate all of the components of the diagnostic device 200 except for the front case 201.

The front case 201 and the rear case 202 can be disposed to face the accommodating portion 203 while the side surfaces are in contact with each other.

The accommodating portion 203 formed by the front case 201 and the rear case 202 is changed from an open space to a closed space according to the opening and closing of the front case 201.

An outer case accommodating the front case 201 and the rear case 202 simultaneously can be further formed. The outer case can be formed in a box type as shown in FIG. 3, can have a handle formed for easy portability, and have a pedestal formed to dispose the diagnostic device 200 at a certain angle.

The bottom surfaces of the front case 201 and the rear case 202 have the same size and define the total area of the biosensor diagnostic device 200.

The bottom surface can be formed in various shapes, and the shape can be a rectangle as shown in FIG. 4, but is not limited thereto, and can be a circle, an ellipse, a rhombus, or the like.

Meanwhile, when the shape of the bottom surface is a rectangle as shown in FIG. 4, the area is a portable size, and in the case of a polygon, one side can satisfy 30 cm or less, but it is not limited thereto, and it can be further miniaturized.

The height of the side surface forming the accommodating portion 203 of the rear case 202 can be greater than the height of the side surface of the front case 201, and the inner cover 205 is formed in the accommodating portion 203 of the rear case 202.

The inner cover 205 has the same shape as the rear case 202 so that it can be inserted into the accommodating portion 203 of the rear case 202, and the bottom surface of the inner cover 205 can have a smaller area than the rear case 202 but can be fitted to minimize a space between the side surface and the bottom surface of the rear case 202 and the side surface and the bottom surface of the inner cover 205.

In addition, since the inner cover 205 is integrated with the rear case 202, one of the two can be omitted. The inner cover 205 serves as a cover that achieves a substantial integration, and when the case 201, 202 is damaged, the inner cover 205 can be separated from the case 201, 202 and replaced.

A plurality of modules are accommodated inside the accommodating portion 203 of the inner cover 205.

A supporter 2081, 2082 for supporting a module while defining the position of each module can be formed on the bottom surface of the inner cover 205, and the supporter 2081, 2082 can be variously designed depending on the disposition of the inner modules. The supporters 2081 and 2082 can be provided in plurality.

The main board 255 is accommodated in the accommodating portion 208 of the inner cover 205.

The main board 255 can be electrically connected to internal modules for executing a plurality of functions, and as shown in FIG. 4, a display module 295 constituting the display unit 290 and the cartridge insertion module 2911 in which the signal conversion amplifier 210 and the sensor controller 240 are integrated can be disposed in the front direction of the main board 255. In addition, a control switch 254 of the user interface of the front panel 291 can be disposed on the front surface.

An operation module 251 and a communication module 261 for controlling the operation of the control device and reading a detection signal according to a program can be disposed on the rear surface of the main board 255.

In addition, a QR reading module 271 can be disposed on the rear surface of the main board 255.

A battery 281 for applying power to the main board 255 and each of the functional modules is disposed, and the battery 281 can be disposed adjacent to the bottom surface of the inner cover 205.

Specifically, the front panel 291 includes a reference plane exposed on the front surface of the biosensor diagnostic device 200 as shown in FIG. 3.

The front panel 291 includes a first opening 292 for exposing a display module 295 that is disposed on the rear surface of the front panel 291 and displays an image on the front surface.

The first opening 292 can be covered with a transparent film, but is not limited thereto, and the display unit 290 of the display module 295 can be directly exposed.

A plurality of buttons, dials, and terminals 294, 296, 297 and the like for a user interface can be disposed around the first opening 291.

The plurality of buttons, dials, terminals 294, 296, 297, etc. can be adjusted in various forms according to design. For example, as shown in FIG. 3, a control dial 2941 can be disposed in a lower side of the first opening 292, and a plurality of terminals and dials 296 and 297 can be disposed also in the left side of the first opening 292, thereby receiving operation commands directly from a user. Alternatively, the cartridge insertion module 2911 can be disposed in the left side of the first opening 292 in the front panel 291, and in the left side of the reference plane.

Meanwhile, the cartridge insertion module 2911 is disposed in the right side of the first opening 292 in the front panel 291, and in the right side of the reference plane.

The cartridge insertion module 2911 protrudes from the reference plane to the front surface and includes a terminal portion to be electrically connected by inserting the connection terminal 153 of the cartridge in the Z-axis direction.

Accordingly, a terminal portion is formed in a side surface of the insertion module 2911, and the terminal portion can include at least one insertion hole 2914.

The insertion hole 2914 can be implemented in various ways depending on the shape of the connection terminal 153 of the cartridge. When the connection terminal 153 of the cartridge is formed in an SD card chip type, a USB type such as USB-A, USB-C type, or a PIN type, correspondingly, it can be formed to read an electrode of the connection terminal 153.

In addition, when the plurality of insertion holes 2914 are formed so as to read various types of connection terminal 153, the plurality of insertion holes 2914 can be disposed in parallel along the X-axis direction in the side surface of the insertion module 2911.

A second opening 293 for exposing the QR reading module 271 is disposed in the lower side of the insertion module 2911.

The second opening 293 is formed in a position aligned with the rear surface of the housing 101 of the cartridge 100 in the X-axis direction in a state in which the connection terminal 153 of the cartridge is inserted into the insertion hole 2914 of the cartridge insertion module 2911.

The second opening 293 can be covered with a transparent film, and the second opening 293 can have a rectangular shape, but an area of the second opening 293 can be smaller than that of the first opening 292. Further, the second opening 293 can have any shape corresponding to a shape of the QR reading module 271 or a QR area 2553.

The second opening 293 serves as a passage through which the QR reading module 271 disposed on the rear surface reads the QR code of the cartridge 100 that is placed on the front surface. In the second opening 293, a light guide part 2912 protruding from the rear surface of the front panel 291 to form a sidewall of the second opening 293 in order to maintain a distance between the QR reading module 271 and the cartridge 100 is formed.

The light guide part 2912 can serve as an illumination for photographing of the QR reading module 271 while maintaining the distance of the QR reading module 271. That is, the light guide part 2912 can include a light guide plate formed on a sidewall of the second opening 293.

A main board 255 in which each module is mounted is disposed on the rear surface of the front panel 291, and the main board 255 can also have a shape similar to the bottom surface of the inner cover 205.

The main board 255 is divided into a display area 2551 in which the display module 295 is disposed in correspondence with e.g., overlapping in a front-rear direction) the area division of the front panel 291, a cartridge area 2552 corresponding to e.g., overlapping in a front-rear direction) the cartridge insertion module 2911, a QR area 2553 corresponding to the second opening 293, and a control area 254 corresponding to e.g., overlapping in a front-rear direction) the button and the dial for a user interface.

The main board 255 is a circuit board on which a circuit is patterned (e.g., layered or printed on) on the front and rear surfaces of the main body 255, and a connection terminal or a connector for electrical connection is disposed in each area. Each functional module can be integrated on the main board 255 after connecting the connection terminal of the board and connector and the connection terminal of each module or connector while being physically fixed in a defined area.

As shown in FIG. 4, a terminal module 241 in which the signal conversion amplifier 210, the signal filtering unit 220, and the sensor controller 240 are integrated is mounted in the cartridge area 2552 of the main board 255 corresponding to the cartridge insertion module 2911. The terminal module 241 can be connected to a insertion hole module 211 into which the connection terminal 153 of the cartridge is inserted by a flexible printed circuit board FPCB 2111, and unlike this, can be implemented as a single (e.g., unitary) component.

In addition, the display module 295 can be an LCD or LED panel module or any known type of display panel disposed in the display area 2551, and a terminal opening 2951 can be formed in the main board 255 in order to connect the operation module 251 on the rear surface of the main board 255 with the battery 281.

The operation unit 250 and the communication module 261 can also be connected to the main board 255 through a connector at the rear surface of the main board 255, but the disposition on the main board 255 is not limited thereto.

Meanwhile, the QR reading module 271 that reads a QR code through a QR opening 2554 formed in the QR area 2553 is disposed on the rear surface of the main board 255, and the QR reading module 271 is also electrically connected to the main board 255 through the flexible printed circuit board FPCB 2711 to receive power and control signals. That is, the QR reading module 271 can include the FPCB 2711 to electrically connect the QR reading module 271 to the main board 255.

A side frame 209 is formed for the disposition and fixing of such modules. The side frame 209 fixes the inner cover 205 and the front panel 291, and the inner cover 205 is fixed to the side frame 209 through a screw hole 2061 (or a plurality of screw holes 2061) extended from one end portion 206 of the side surface. Further, the side frame 209 is provided with multiple screw holes 2091 that overlap the screw holes 2061 of the inner cover 205. Fasteners, such as screws or bolts, pass through the screw home 2091 of the side frame 209, then are fixed to the screw holes 2061 of the inner cover 205. Each module is fixed at a specific position on the main board 255 through a plurality of other fixing parts, the main board 255 is physically fixed by coupling a screw and a screw hole between a plurality of fixing protrusions 2081 and 2082 protruding from the bottom surface of the inner cover 205 and the front panel 291.

Each module and component disposed therebetween is fixed by fixing the main board 255, the front panel 291, and the inner cover 205, and an electrical connection is maintained without being shaken during movement.

In addition, the front panel 291 and the inner cover 205 are fixed together through the screw hole and the screw of the side frame 209 to be integrated. Fixing and assembling of each component proceeds by the screw hole and the screw, thereby making it easy to disassemble and reassemble.

The front case 201, the rear case 202, the inner cover 205, and the front panel 291 can be formed of a resin such as polycarbonate or plastic for portability and reduced weight.

The biosensor diagnostic device 200 is, as shown in FIG. 3, provided to a user by exposing the front panel 291 in a form of having a space for accommodating a plurality of modules therein, and various external cases can be applied.

In particular, in the reference plane of the front panel 291 provided to a user as shown in FIG. 3, a screen of the display module 295 is provided, and various buttons and dials for a user interface are provided. In particular, a power button, a plurality of control buttons, and a USB terminal can be provided. In addition, the cartridge insertion module 2911 is provided to one side of the display module 295, and the connection terminal 153 is inserted into the insertion hole 2914 parallel to the reference plane of the panel 291, so that diagnosis of the biosensor cartridge 100 is possible.

Hereinafter, the biosensor cartridge 100 applied to the present embodiment will be described with reference to FIGS. 5 to 11.

Figure 5A:
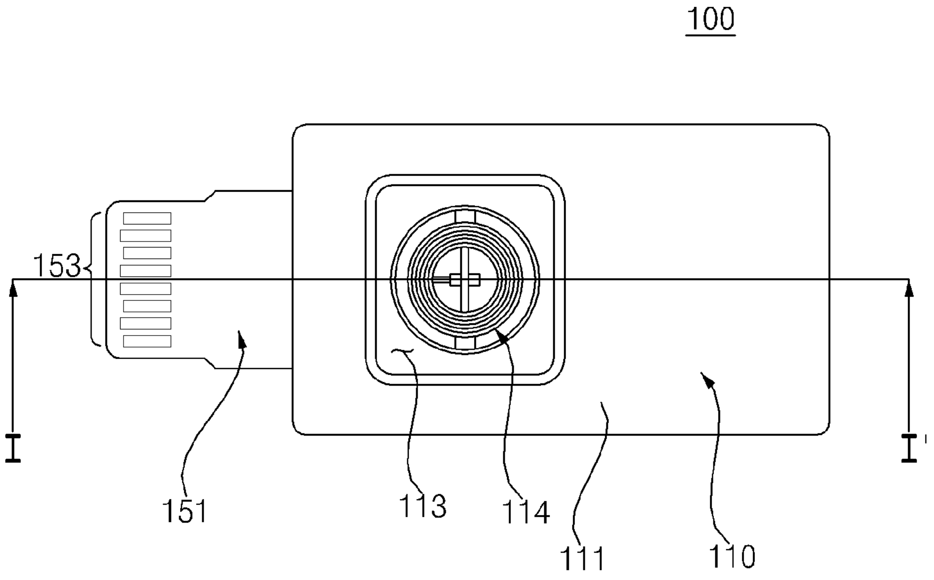
FIGS. 5A and 5B are respectively top and rear views of an example of the biosensor cartridge of FIG. 1.
Figure 5B:
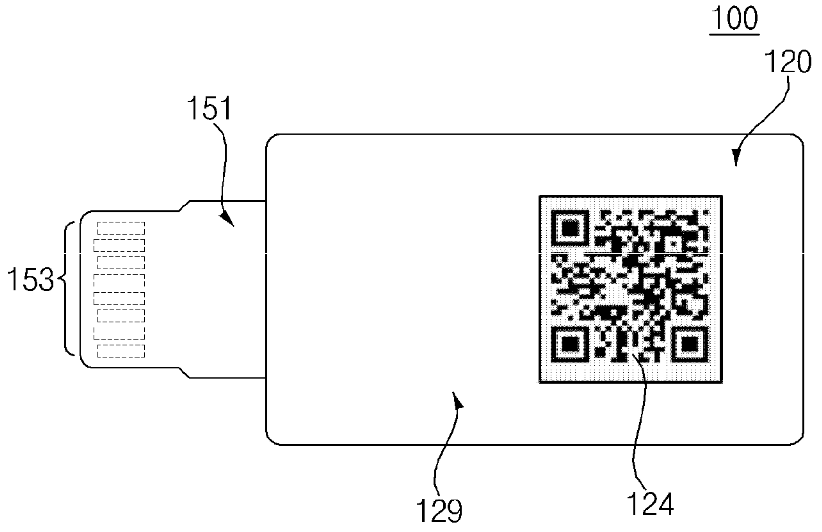
Figure 6:
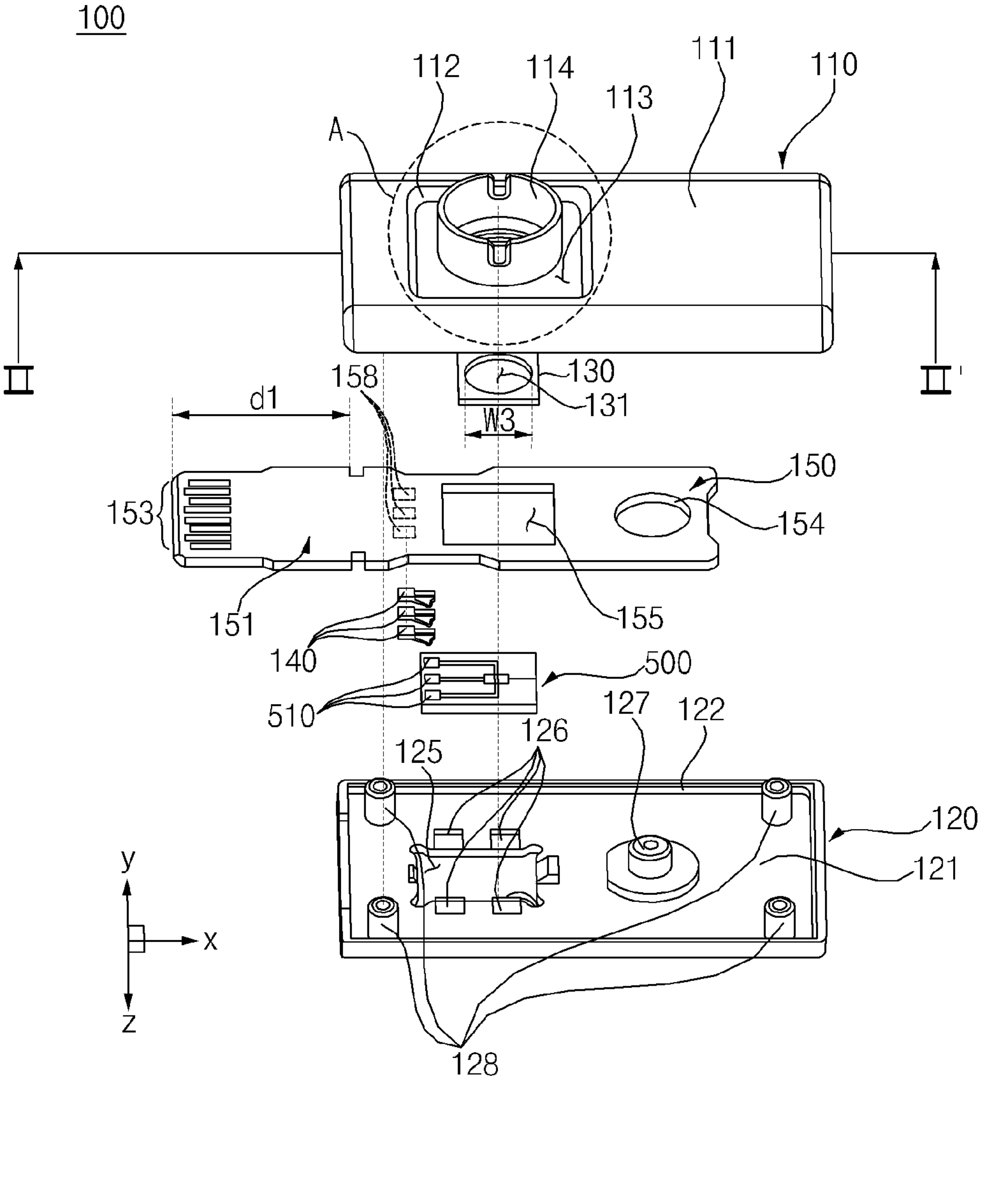
FIG. 6 is an exploded perspective view of an example of the biosensor cartridge of FIG. 1.
Figure 7:
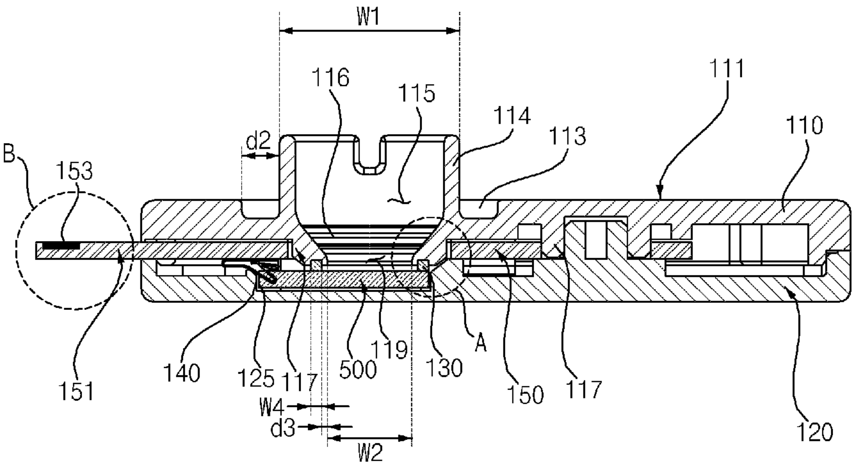
FIG. 7 is a cross-sectional view of the biosensor cartridge taken along lines I-I' of FIG. 5A and II-II' of FIG. 6.
Figure 8:
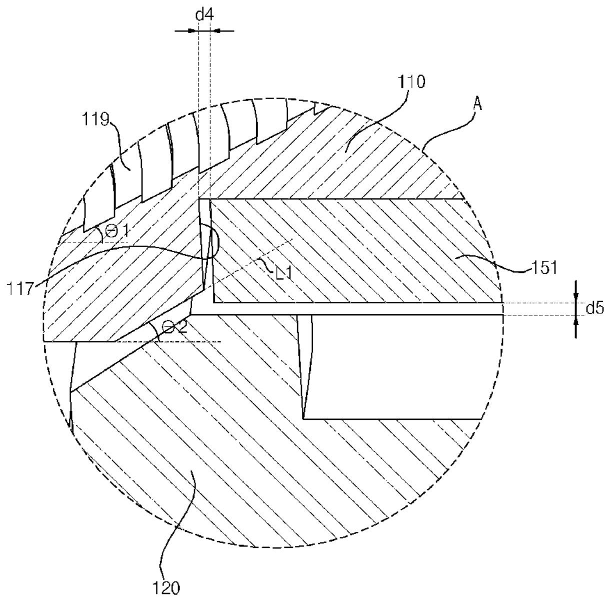
FIG. 8 is an enlarged view of area A of FIG. 7.
Figure 9:
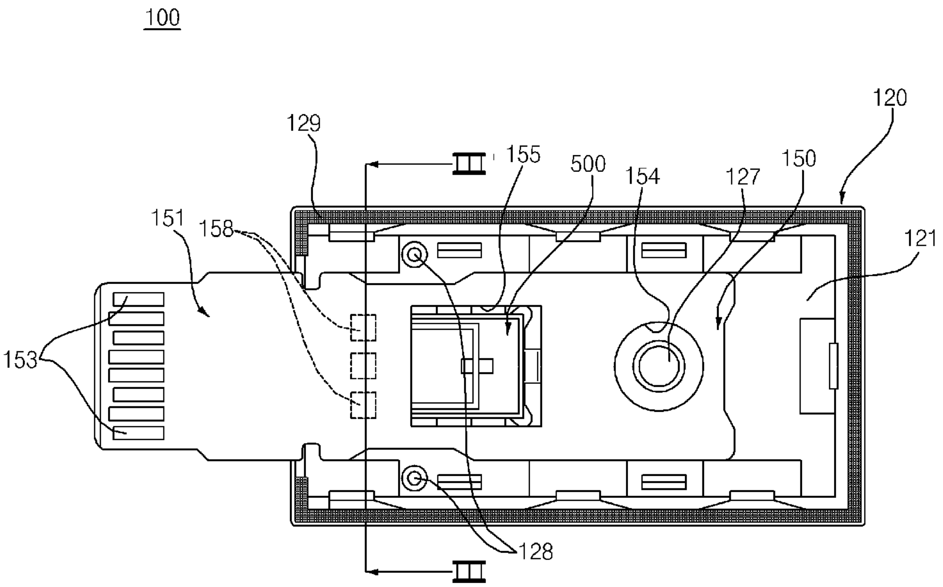
FIG. 9 is a transparent drawing seen through the upper housing of the biosensor cartridge of FIG. 6.
Figure 10:
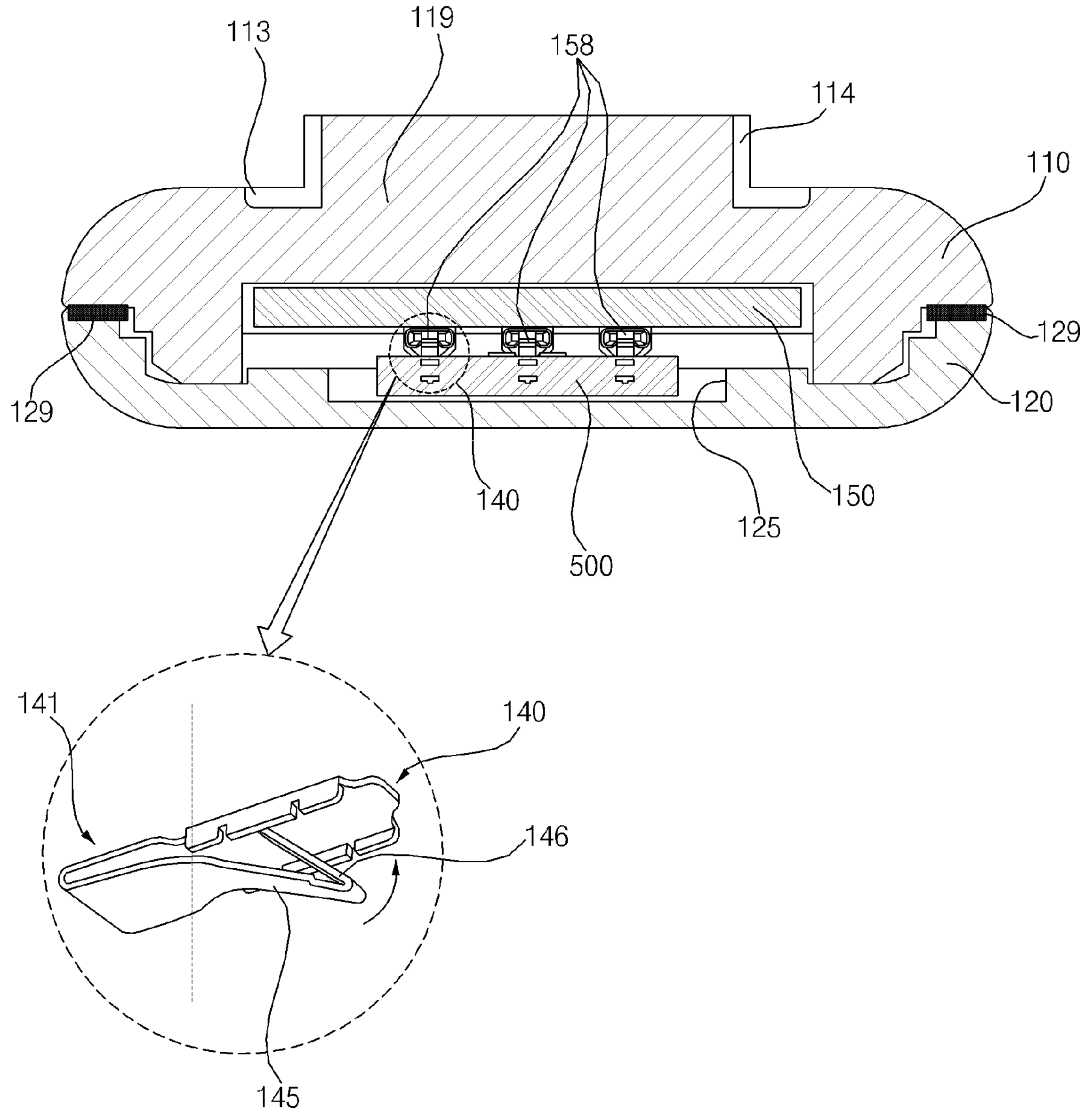
FIG. 10 is a cross-sectional view of the biosensor cartridge taken along line III-III' of FIG. 9.
Figure 11:
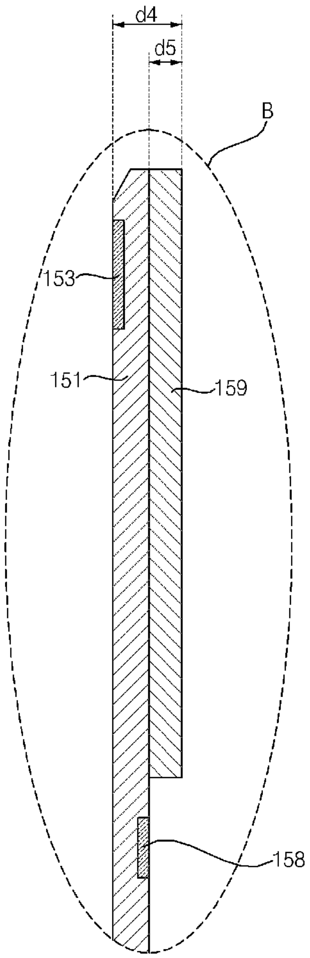
FIG. 11 is a cross-sectional view of area B of FIG. 9, illustrating a connection terminal of the biosensor cartridge.

FIGS. 5A and 5B are top and rear views of an example of the biosensor cartridge 100 of FIG. 1, FIG. 6 is an exploded perspective view of an example of the biosensor cartridge 100 of FIG. 1, and FIG. 7 is a cross-sectional view of the biosensor cartridge 100 of FIGS. 5 and 6 taken along lines I-I' and II-II'. At this time, FIG. 8 is an enlarged view of area A of FIG. 7, FIG. 9 is a transparent drawing seen through the upper housing of the biosensor cartridge of FIG. 6, FIG. 10 is a cross-sectional view of the biosensor cartridge of FIG. 9 taken along line III-III', and FIG. 11 is a cross-sectional view of area B of FIG. 9, illustrating a connection terminal of the biosensor cartridge.

Referring to FIGS. 5A to 11, the biosensor cartridge 100 according to the present embodiment accommodates a sensor chip 500 that generates an electrical detection signal according to a target material and has a structure of including a connection terminal 153 capable of transmitting the detection signal to an external diagnostic device 200.

Specifically, the biosensor cartridge 100 is formed of a bar type housing 110, 120, a partial surface 151 of the circuit board 150 protrudes from the end surface of the side surfaces of the housing 110, 120, and a connection terminal 153 that is inserted into the external diagnostic device 200 and transmits the detection signal is formed on the partial surface 151 of the protruding circuit board 150.

The accommodating portion 119 for accommodating a specimen is formed on an upper surface 111 of the housing 110, 120, and a QR label 124 can be attached to the lower surface of the housing 110, 120.

The connection terminal 153, which protrudes from the side surface of the housing 110, 120 and is exposed, is disposed in the same direction as the lower surface of the housing 110, 120 and is not exposed when the cartridge 100 is viewed from the upper surface. Accordingly, it is possible to reduce the risk that the specimen flowing out of the accommodating portion 119 touches the connection terminal 153.

The biosensor cartridge 100 includes housing 110, 120, a sensor chip 500, and a circuit board 150.

The circuit board 150 is also formed in a bar type and has one end where a connection terminal 153 is formed so that the connection terminal 153 of the circuit board 150 is coupled to be exposed to the outside of the housing 110, 120, thereby forming the entire shape of cartridge 100.

Specifically, the housing 110, 120 includes a lower housing 120 and an upper housing 110.

The lower housing 120 includes a bar-type bottom surface 121 (e.g., a planar shaped surface or a rectangular shape surface that is planar) and a side surface 122 surrounding the bottom surface 121. The bottom surface 121 includes a plurality of coupling protrusion 127, 128 protruding toward the upper housing 110, and the coupling protrusion 127, 128 is fitted with a coupling groove of the upper housing 110 so that the upper and lower portions of the housing 110, 120 are coupled and integrated. The lower housing 120 can include four coupling protrusions 128 positioned at corners of the lower housing 120, which are coupled to corresponding grooves of the upper housing 110 which are located at corners of the upper housing 110. The coupling protrusion 127 (e.g., substrate protrusion) can be from the other coupling protrusions 128 (e.g., corner coupling protrusions 128). Alternatively, more than four coupling protrusions 127 can be formed and the coupling protrusions can be equally spaced around a periphery of the lower housing 120.

A substrate protrusion 127 defining a position while fixing the circuit board 150 toward the upper housing 110 is formed on the bottom surface 121 of the lower housing 120, and a plurality of sensor protrusions 126 defining a chip area 125 in which the sensor chip 500 is disposed are formed in one side of the lower housing 120, the one side facing the upper housing 11.

The sensor protrusion 126 is disposed to correspond to the size of the sensor chip 500 so as to define a chip area 125 in which the sensor chip 500 is disposed and is formed to have a certain elasticity (e.g., predetermined elasticity) so that the sensor chip 500 can be fitted. However, since the sensor protrusion 126 does not electrically connect the sensor chip 500, it can be implemented in various forms and can be formed as a rail structure for sliding coupling in addition to fitting.

A sensor chip 500 is disposed in the chip area 125.

The sensor chip 500 is a semiconductor-based biosensor and is divided into a sensor area 540 that reacts according to a target material in the specimen through contact with the specimen, and a pad area 510 for transmitting a detection signal generated according to the sensor area 540 to the circuit board 150.

The pad area 510 can be patterned to be disposed in one side of the sensor chip 500 as shown in FIG. 6, and accordingly, the electrical connection between the circuit board 150 and the sensor chip 500 is performed in the pad area 510.

The sensor chip 500 can have different sizes depending on the size of the cartridge, for example, can have a rectangular shape of 8 mm*6 mm, or can have a square shape of 6 mm*6 mm. The size of the sensor chip 500 can be variously implemented according to the performance of the sensor chip 500 or the purpose of the sensor chip 500.

The detailed structure of the sensor chip 500 will be described in detail later.

The circuit board 150 is disposed on the sensor chip 500.

The circuit board 150 can be provided as a rigid board like a printed circuit board (PCB), and the sensor chip 500 is electrically/physically bonded to the lower portion.

The circuit board 150 includes a sensor opening 155 (e.g., opening) through which a sensor area 540 of the sensor chip 500 is exposed, and the sensor opening 155 has a size smaller than that of the sensor chip 500. In addition, the opening 155 can have a size corresponding to the sensor area 540 of the sensor chip 500 and has a size to expose the sensor area 540.

The circuit board 150 further includes a protrusion hole 154 through which the substrate protrusion 127 of the lower housing 120 penetrates to fix the circuit board 150, and accordingly, the circuit board 150 and the lower housing 120 are fixed.

The circuit board 150 can be implemented by a plurality of circuit patterns patterned on a base member (not classified by reference numerals, denoted by 150 in the drawing) as the deposition structure thereof, and an insulating layer covering the circuit pattern.

The circuit pattern and the insulating layer can be formed on the front surface of the base member, and a reinforcing plate 159 can be attached to the rear surface of the base member.

At this time, the rear surface of the base member can be defined as a surface facing the lower housing 120, and the front surface of the base member can be defined as a surface facing the upper housing 110.

In other words, on the rear surface of the circuit board 150, a circuit pattern including a plurality of connection pads 158 for connecting to the sensor chip 500 is formed, and a circuit pattern that extends to the connection pad 158 to transmit the detection signal from the connection pad 158 to the external diagnostic device 200 is formed to be connected to the connection terminal 153 of the front surface.

Accordingly, the number of connection terminal 153 on the front surface of the circuit board 150 can be equal to or greater than the number of pads of the sensor chip 500.

The plurality of connection terminals 153 can be spaced apart from each other at one end of the exposed surface 151 of the circuit board 150, i.e., at one end of the circuit board 150 and disposed in parallel.

For example, when the sensor chip 500 has three pads, the number of the connection pads 158 of the circuit board 150 also satisfies three, and the number of the connection terminal 153 satisfies three or more.

The connection terminal 153 further includes terminals not electrically connected to each connection pad 158 and can be used as a terminal for electrostatic discharge (ESD) blocking.

As shown in FIG. 9, the circuit pattern patterned on the front surface of the circuit board 150 can include eight connection terminals 153. In such a connection terminal 153, when the sensor chip 500 is driven in multi-channel to be connected to a plurality of connection pads 511 (e.g., electrode pads) and to transmit and receive signals, four connection terminals can be allocated as a connection terminal 153 for transmitting and receiving signals of each pad by connecting to the source pad, drain pad, and gate pad of the sensor chip 500 corresponding to each channel, and four connection terminals are applicable as a terminal for ESD and incoming detection signal generation.

Such a connection terminal 153 can be formed as an SD card pin type or a USB-A type depending on an embodiment, but a USB-C type having more terminals can also be utilized. Preferably, the connection terminal 153 can be implemented as a pin type, and more terminals can be implemented.

Thus, the number of pads of the connection terminal 153 can increase in proportion to the number of probe material applied to the sensor chip 500, i.e., the number of source electrodes (or the number of drain electrodes).

On the other hand, as shown in FIG. 11, a reinforcing plate 159 can be further included on the rear surface of the circuit board 150, that is, on the surface facing the lower housing 120, and the reinforcing plate 159 of FIG. 11 can be attached to the rear surface of the base member of the circuit board 150 to improve the rigidity of the circuit board 150.

The circuit board 150 extends to the connection terminal 153, and the connection terminal 153 is inserted by applying a physical force to the insertion module 2911 of an external diagnostic device 200, by which diagnosis is made.

Therefore, a physical force for insertion of the connection terminal 153 is applied to the circuit board 150, and the circuit board 150 requires rigidity such that the circuit board 150 is not bent (e.g., is minimally bent) even when the force is applied.

Since the base member of the circuit board 150 has a thin thickness of 0.3 to 0.5 mm, an insulating base member can be a flexible circuit board.

By attaching a reinforcing plate 159 for reinforcing rigidity to the rear surface of the circuit board 150 having such flexibility, the overall rigidity of the circuit board 150 is improved.

The base member of the circuit board 150 can be implemented with a flexible resin such as polyimide, and a sheet of a general, flexible circuit board can be applied.

At this time, the reinforcing plate 159 can be adhesively fixed to the base member using a double-sided tape, and the reinforcing plate 159 can have a fifth thickness d5.

The fifth thickness d5 of the reinforcing plate 159 can range from 0.3 to 0.4 mm, and thus the overall thickness d4 of the circuit board 150 can range from 0.6 to 0.9 mm; preferably, the overall thickness can range from 0.8 to 0.9 mm but is not limited thereto.

The reinforcing plate 159 can be made of a rigid material having the fifth thickness d5, for which Al or SUS cut according to the shape of the circuit board 150 and attached to the base member by the double-sided tape can be applied. In addition, the reinforcing plate 159 can allow electroless processing through anodizing to ensure insulation while maintaining rigidity. On the other hand, resins such as FR4 or PI can be applied and can be appropriately substituted according to thickness and strength.

As described above, by attaching the reinforcing plate 159 to the rear surface of the circuit board 150, the required strength when a part of the circuit board 150 is used as the connection terminal 153 inserted into the diagnostic device 200 can be satisfied.

Meanwhile, the circuit board 150 includes a plurality of coupling grooves, and the plurality of coupling grooves are formed to be able to fit while specifying a position when the upper housing 110 and the lower housing 120 are coupled.

Meanwhile, the upper housing 110 has a structure where the upper surface 111 and the rear surface are different from each other as shown in FIG. 6.

The upper housing 110 faces the lower housing 120 and is coupled to the lower housing 120 and serves as an upper case capable of accommodating the circuit board 150 and the sensor chip 500 therein. In addition, an accommodating portion 119 exposing the sensor area 540 of the sensor chip 500 is formed in the upper housing 110 to accommodate a test target specimen.

The upper housing 110 is formed to have rigidity that can firmly support the connecting member 140 by pressing the connecting member 140 with a certain force. The connecting member 140 can be formed in plurality and can be conductive tabs (e.g., metal tabs) for connecting the connection pad 158 disposed on the circuit board 150 with the pads 511 of the sensor chip 500.

The upper housing 110 and the lower housing 120 can be configured to surround the sensor chip 500 and the circuit board 150 to protect the sensor chip 500 and the circuit board 150 from the outside. At this time, when the upper housing 110 is coupled to the lower housing, an opening that protrudes the connection terminal 153 of the circuit board 150 to the end side is formed on the cross-sectional surface to expose the connection terminal 153 to the cross-sectional surface. Thus, the connection terminal 153 is inserted into the insertion hole 2914 of an external diagnostic device 200 as the connection terminal 153 of the cartridge. Due to firm coupling between the upper housing 110 and the lower housing 120, a specimen provided to the sensor chip 500 through the accommodating portion 119 can be prevented from leaking into the housing 110, 120.

The accommodating portion 119 for exposing the sensor area 540 of the sensor chip 500 and accommodating a specimen is formed on the upper surface 111 of the upper housing 110. The accommodating portion 119 is a space for inducing a reaction with the exposed sensor area 540 by accommodating a test target specimen in a fluid state, e.g., in a liquid state, and the accommodating portion 119 forms a conical channel whose diameter becomes narrower as it approaches the sensor area 540 from the upper surface 111.

The accommodating portion 119 is formed to have an inclined surface 116 such that a diameter w1 of the opening of the upper surface is larger than a diameter w2 of the opening at the distal end of the accommodating portion 119.

The diameter w2 of the opening at the distal end of the accommodating portion 119 can be 3 mm to 6 mm. Preferably, it can satisfy 3.8 to 4.5 mm, more preferably 4 mm to 4.3 mm. However, it is not limited thereto and can be variable depending on the overall size of the cartridge 100 and the size of the sensor chip 500.

At this time, a first inclination angle 81 of the inclined surface 116—the angle of the inclined surface 116 with respect to the horizontal direction (x-axis) in which the sensor chip 500 is placed, when viewed from the cross section in FIG. 7—can be uniform, but can have an inflection point.

That is, the inclination angle increases as it approaches the sensor area 540, and it forms a verticality in the outermost area closest to the sensor area 540, so that it can be changed to a cylindrical passageway.

As described above, since the accommodating portion 119 has the inclined surface 116, a concave groove having a depth that is a height from the upper surface of the upper housing 110 to the sensor area 540 is formed. A specimen is collected in the groove to induce a reaction with the probe material in the sensor area 540.

Meanwhile, the accommodating portion 119 further includes a guard 114 for preventing the specimen of the accommodating portion 119 from flowing to the outside as shown in FIGS. 5A, 6, and 7. The guard 114 can be formed in a cylindrical shape, and is formed to surround the opening of the upper surface 111 of the upper housing 110 and protrude upward (in the y-axis) from the upper surface 111. The guard 114 can extend away from the upper surface 111, in a direction perpendicular to the upper surface 111 (e.g., an extension direction of the upper surface 111).

Accordingly, the diameter W1 of the guard 114 can be the same as the diameter of the opening of the upper surface 111.

A guard groove 113 of a certain depth is formed on the upper surface 111 of the upper housing 110 while surrounding the accommodating portion 119. The guard groove 113 is to prevent the specimen overflowing from the accommodating portion 119 from flowing out of the housing 110 and is formed to be recessed by a certain depth from the upper surface 111.

The guard groove 113 can be formed in a circular shape identical to the shape of the guard 114 but can be formed in a rectangular shape having a minimum distance d2 or more from the guard 114 as shown in FIG. 6.

As described above, the accommodating portion 119, where the specimen and the sensor area 540 contact each other, firstly has a concave cup shape to accommodate the specimen and provides a space where the target material of the specimen and the probe material of the sensor area 540 react with each other. In addition, the accommodating portion 119 forms a guard 114 surrounding the opening of the upper surface 111 to secure the amount of the specimen by accommodating the overflowing specimen secondarily, and to prevent the risk of exposing the specimen to the outside.

In addition, tertiarily, the guard groove 113 is formed around the guard 114 to accommodate the specimen when the specimen overflows the guard 114 or flows to the outside of the guard 114, thereby preventing the specimen that can contain hazardous substances from exposing to the outside.

Thus, the test can be safely performed by changing the shape of the accommodating portion 119 for accommodating the specimen in the upper housing 110.

Meanwhile, the rear surface of the upper housing 110 can include an inclined portion along the inclined surface 116 of the accommodating portion 119.

Accordingly, as shown in FIG. 9, the sensor area 540 of the sensor chip 500 is exposed upward by the sensor opening 115 of the circuit board 150, and the lower opening of the accommodating portion 119 aligns with the exposed sensor area 540.

Therefore, as shown in FIG. 8, the opening 115 of the circuit board 150 is fitted to surround the rear surface of the inclined surface 116 of the accommodating portion 119, thereby fixing the positions of the circuit board 150 and the upper housing 110.

In addition, to this end, the rear surface of the inclined surface 116 of the accommodating portion 119 is formed to have a vertical step 117 in an area where it meets the opening 115 of the circuit board 150.

That is, the rear surface of the inclined surface 116 of the accommodating portion 119 forms an inclined portion along the inclined surface 116 at an angle equal to θ1 or greater θ2 than the inclination angle of the inclined surface 116 of the accommodating portion 119 and is inclined at an angle equal to or greater than the inclined surface 116 to form a space coupled to the circuit board 150.

At this time, at a portion to which the opening 155 of the circuit board 150 is coupled, a step 117 corresponding to the cut surface of the opening 155 of the circuit board 150 can be formed for fitting with the opening 155 of the circuit board 150.

The step 117 can have a separation distance having a fourth width d4 from the side surface of the opening 155 of the circuit board 150, but is not limited thereto, and can be fitted and coupled.

It is easy to fix the circuit board 150 in case of being fitted and coupled without a separation distance, but a separation distance can be formed for tolerance. At this time, the fourth width d4 of the separation distance is required to range from 0.05 to 0.2 mm.

In addition, when the rear surface of the circuit board 150 is placed in the lower housing 120, a fifth width d5 can be ensured from the rear surface of the upper housing 120 as a separation distance for tolerance. At this time, the fifth width d5 of the separation distance is required to range from 0.05 to 0.2 mm, which is the same as the fourth width d4.

As described above, the front surface of the circuit board 150 and the rear surface of the upper housing 110 can be coupled with a certain tolerance distance to prevent distortion of the circuit board 150, and to be applied as a buffer for an error in the process to reduce the defect rate.

In addition, even if the separation distance for such a tolerance is included, the circuit board 150 and the housing 110, 120 can be clearly coupled by combining with the upper and lower housings 110 and 120 by a plurality of coupling grooves and coupling holes.

Accordingly, the circuit board 150 is firstly fixed while the step 117 of the rear surface of the accommodating portion 119 and the sensor opening 115 of the circuit board 150 are fitted and is secondarily fixed while the fixing protrusion 127 of the lower housing 120 and the fixing hole 154 of the circuit board 150 are coupled, so that the position is specified.

Meanwhile, a sealing part 130 can be further formed between the upper housing 110 and the sensor area 540.

The sealing part 130 is formed as a separate element as shown in FIG. 6 and is coupled and compressed at the time of the housing 110, 120 coupling, thereby preventing the specimen from flowing to the outside of the sensor area 540.

In this case, the sealing part 130 can have a sealing opening 131 having a diameter w3 larger than the diameter w2 of the rear opening of the accommodating portion 119 as shown in FIG. 7, and the rear opening and the sealing opening 131 can be disposed to have a concentric circle. Accordingly, when assembling, as shown in FIG. 7, the sealing part 130 is disposed outside the lower opening of the accommodating portion 119 to form a concave groove.

This is designed to avoid danger that the elastic sealing part 130 is pushed to the sensor area 540 by the compression of the sealing part 130 and covers the sensor area 540 in contact with the specimen, as a tolerance is set when the sealing part 130 is compressed.

As described above, it is possible to ensure the sealing of the specimen while securing the area of the sensor area 540 by adjusting the size of the sealing opening 131 of the sealing part 130 and the opening size of the accommodating portion 119.

Meanwhile, the sealing part 130 can be a closed cell type waterproof pad having elasticity but is not limited thereto.

Meanwhile, the connection pads 158 formed on the rear surface of the circuit board 150 is formed in the same number as the pad 511 of the sensor chip 500, and a connecting member 140 is disposed for electrical and physical connection between the connection pads 158 of the circuit board 150 and the pad 511 of the sensor chip 500.

As shown in FIG. 10, the connecting member 140 can be formed separately for each pad 158 and can be formed as a clip-type elastic (e.g., deformable) contact piece. Such a connecting member 140 can be a C-clip or a spring terminal.

Each connecting member 140 can include a first surface 141 in contact with the pad area 510 of the circuit board 150 and a second surface 145 configured to be elastically deformable by being bent in the longitudinal direction of the first surface 141 from one side surface of the first surface 141.

The first surface 141 is formed to have a certain length (e.g., predetermined length) and is in contact with the pad area 510 of the circuit board 150, and the second surface 145 is in contact with the pad 511 of the lower sensor chip 500 and elastically deformed.

Such a connecting member 140 is elastically deformed at the bending portion 146, which is a bent portion 146 between the first surface 141 and the second surface 145. When pressure is applied vertically between the lower portion of the first surface 141 and the upper portion of the second surface 145, the first surface 141 comes into contact with the connection pads 158 of the circuit board 150. The second surface 145 comes into contact with the pad 510 of the sensor chip 500.

To this end, in a state where the connection pads 158 of the circuit board 150 and the first surface 141 are in contact with each other through welding or soldering, when the circuit board 150 is disposed in the lower housing 120 in which the sensor chip 500 is disposed, a bending portion 146 is elastically deformed as pressure is applied vertically to the connecting member 140 by assembling the upper housing 110 and the lower housing 120.

At this time, the angle is changed so that the second surface 145 is parallel to the first surface 141, as a spring coupling portion is pushed into the inside of the second surface 145. Thus, the second surface 145 is in contact with the pad 510 of the sensor chip 500 to maintain a conducting state, so that physical coupling and electrical coupling occur simultaneously.

As described above, since the probe material in the sensor chip 500 is not exposed to high temperature in a bonding process by performing electrical connection of the sensor chip 500 with the circuit board 150 without a separate bonding process, it is possible to prevent a problem that protein modification occurs.

That is, in the presence of probe material vulnerable to heat due to the characteristics of the biosensor, the characteristics of the probe material can be maintained by excluding a heating process, and electrical connection between the sensor chip 500 and the circuit board 150 becomes possible.

Meanwhile, on the rear surface 129 of the lower housing 120 of the biosensor cartridge 100, i.e., the rear surface 129 of the cartridge 100 exposed to the outside, a QR label 124 including a QR code in which sensor information including a product ID and a manufacturing serial number for genuine product certification of the biosensor cartridge 100 is stored is attached.

The QR code can be attached to the central area of the rear surface 129 of the lower housing 120 so that the rear surface 129 of the lower housing 120 of the cartridge 100 can be aligned over the second opening 293 which is the QR opening when the cartridge 100 is coupled with the external diagnostic device 200.

The QR code can include all sensor information for genuine product certification. As an example, it can include sensor chip 500 information and cartridge information as well as the product ID and manufacturing serial number. The information of the sensor chip 500 can include probe material activated in the sensor chip 500, a disease to be diagnosed, a manufacturing date, a manufacturing location, and a manufacturing serial number of the sensor chip 500. In addition, the cartridge information can include an assembly date, a test date, and a sensor ID of the biosensor cartridge 100.

The stored QR code is read from the QR reading module 271 of the diagnostic device 200 at the same time when it is inserted into the diagnostic device 200, and a process for genuine product certification can be performed with the cloud server 400.

The biosensor cannot determine whether it is an imitation or not. Even if it is genuine, sensor errors are often found or decided from test data accumulated after manufacturing and sales. Therefore, a process of classifying the biosensor cartridge 100 in which an error has occurred is required before the test proceeds.

In the case of the biosensor cartridge 100, it is possible to check an error including a current risk to a corresponding type of the biosensor cartridge 100 through such a certification procedure.

The biosensor cartridge 100 according to the present embodiment does not include a separate memory chip for storing sensor-specific information for such a certification procedure.

When such a memory chip is separately included, the size of the circuit board 150 increases, and the size of the housing 110, 120 increases according to the size of the circuit board 150. In addition, as the circuit of the circuit board 150 becomes complicated, the number of pins used in the connection terminal 153 increases, thereby causing problems in miniaturization and cost of the cartridge 100.

Like the biosensor cartridge 100 according to the present embodiment, by attaching a QR label 124 on which a QR code is printed to the rear surface of the housing, such a memory chip can be replaced (e.g., a memory chip is not necessary), and the time difference between reading of the sensor result and certification can be minimized by reading the QR code almost simultaneously (e.g., simultaneously) with the coupling of the cartridge 100 and the diagnostic device 200.

Such a QR code can be prevented from being arbitrarily attached and detached by attaching it as a security label 124 such as a VOID label on the rear surface of the lower housing 120.

In such a biosensor cartridge 100, in a state in which the sensor chip 500 is placed in the lower housing 120, the upper housing 110 coupled to the circuit board 150 to which the connecting member 140 is attached is pressed for assembling with the lower housing 120, so that the sensor chip 500 and the circuit board 150 are physically and electrically attached and fixed.

In this case, the attachment of the upper housing 110 and the lower housing 120 can be further reinforced by performing fusion on an edge attachment area 129 of the upper housing 110 and the lower housing 120 as shown in FIG. 10.

Such fusion can be performed by ultrasonic fusion, but is not limited thereto, and can be performed through a separate adhesive member.

The edge attachment area 129 formed as described above is continuously formed in the entire edge excluding an open portion through which the connection terminal 153 protrudes, i.e., at the end of the side surfaces of the upper housing 110 and the lower housing 120, thereby preventing moisture or foreign substances from penetrating into the interior from the outside.

Figure 12:
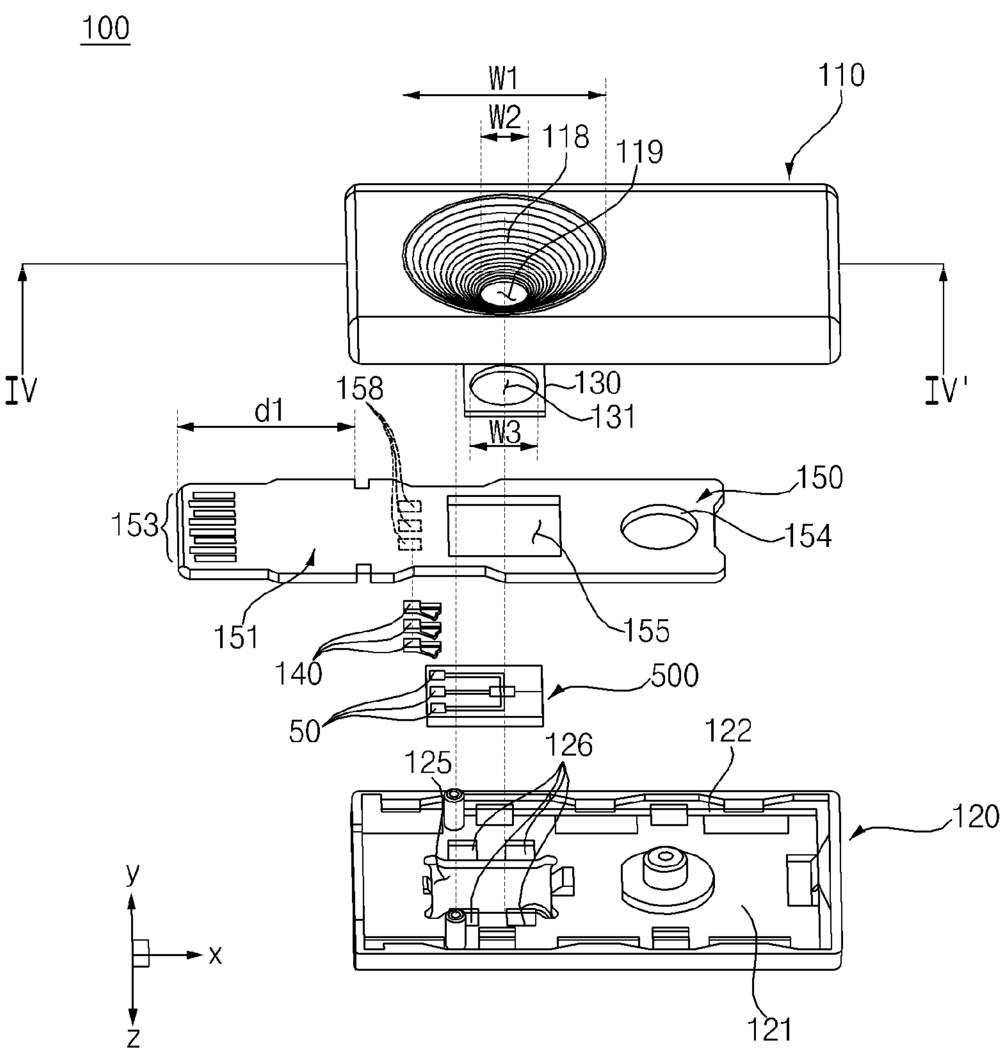
FIG. 12 is an exploded perspective drawing of another example of the biosensor cartridge of FIG. 1.
Figure 13:
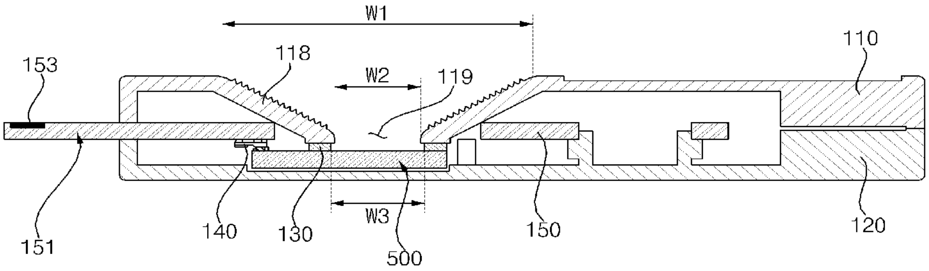
FIG. 13 is a cross-sectional view of the biosensor cartridge taken along line IV-IV' of FIG. 12.

Such a biosensor cartridge 100 can be changed to a configuration shown in FIGS. 12 and 13.

A biosensor cartridge 100 according to the second embodiment can be configured as shown in FIGS. 12 and 13.

FIG. 12 is an exploded perspective view of another example of the biosensor cartridge 100 of FIG. 1, and FIG. 13 is a cross-sectional view of the biosensor cartridge 100 of FIG. 12 taken along line IV-IV'.

In the biosensor cartridge 100 of FIGS. 12 and 13, since the configuration of the lower housing 120, the sensor chip 500, and the circuit board 150 is the same as that of the biosensor cartridge 100 of FIGS. 6 and 7, and the attachment configuration of the upper housing 110 and the lower housing 120 is also the same as FIG. 10, a description thereof is omitted.

In the biosensor cartridge 100 of the second embodiment, the accommodating portion 119 can be formed differently from the first embodiment.

Referring to FIGS. 12 and 13, in the biosensor cartridge 100 according to the second embodiment, the accommodating portion 119 for accommodating the specimen in the upper housing 110 and guiding it to the sensor area of the lower sensor chip 500 is formed.

Specifically, the accommodating portion 119 is a space for receiving a sample inducing a reaction of the sample with the exposed sensor area 540 by accommodating a test target specimen in a fluid state, e.g., in a liquid state, and the accommodating portion 119 is concavely recessed from the upper surface to form a conical passage, i.e., a channel, the diameter of which becomes narrower as it approaches the sensor area 540.

Accordingly, the accommodating portion 119 is formed to have an inclined surface 118 such that the diameter W1 of the opening of the upper surface is larger than the diameter of the opening W2 at the distal end of the accommodating portion 119.

In the accommodating portion 119, since the diameter W1 of the opening of the upper surface is expanded to be wider than the area of the sensor chip 500, the difference between the diameter W1 of the opening of the upper surface and the diameter W2 of the opening at the distal end of the accommodating portion 119 is significantly large.

For example, the diameter W1 of the opening of the upper surface can satisfy (e.g., be) two to three times the diameter W2 (e.g., two to three times larger than the diameter W2) of the opening at the distal end of the accommodating portion 119.

As the difference between the diameter W1 of the opening in the upper surface and the diameter W2 of the opening at the distal end of the accommodating portion 119 becomes larger, the accommodating volume of the accommodating portion 119 increases, so that a large amount of specimen can be accommodated.

At this time, the inclination angle of the inclined surface 118—the angle of the inclined surface with respect to the horizontal direction in which the sensor chip 500 is placed when viewed from the cross section in FIG. 13, can be uniform, but can have an inflection point.

That is, the inclination angle increases as it approaches the sensor area 540, it forms a verticality in the outermost area closest to the sensor area 540, so that it can be changed to a cylindrical passageway.

As described above, since the accommodating portion 119 has the inclined surface 118, a concave groove having a depth that is a height from the upper surface of the upper housing 110 to the channel area is formed. A specimen is collected in the groove to induce a reaction with the probe material in the sensor area 540.

As described above, the biosensor cartridge 100 accommodates the biosensor chip 500 inside the housing 110, 120, and is provided to accommodate the circuit board 150 for transmitting the detection information of the sensor chip 500 to the external diagnostic device 200.

Hereinafter, the biosensor chip 500 of the present embodiment will be described with reference to FIGS. 14 to 17.

Figure 14:
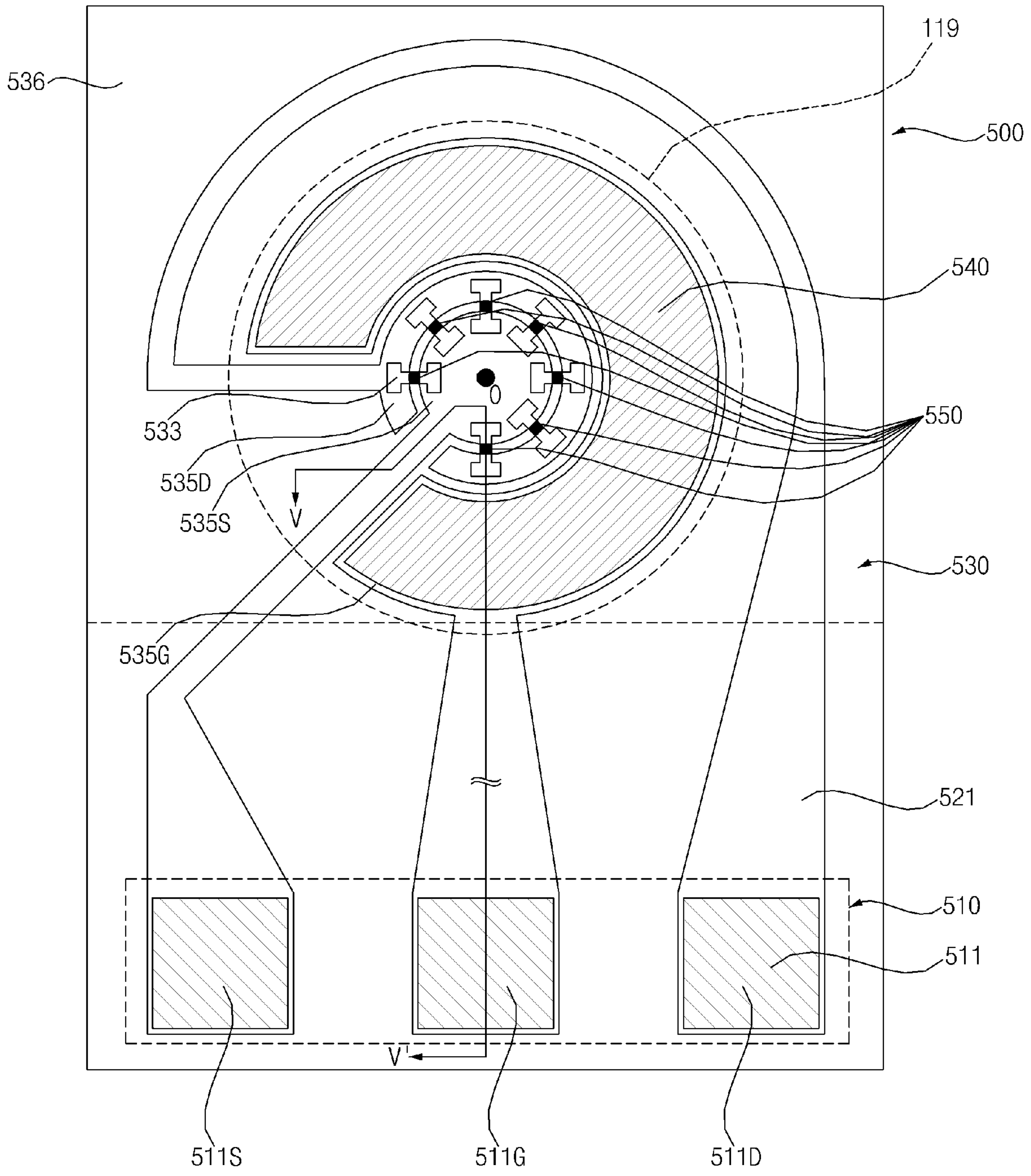
FIG. 14 is a top view of one example of a sensor chip applicable to FIGS. 6 and 12.
Figure 15:
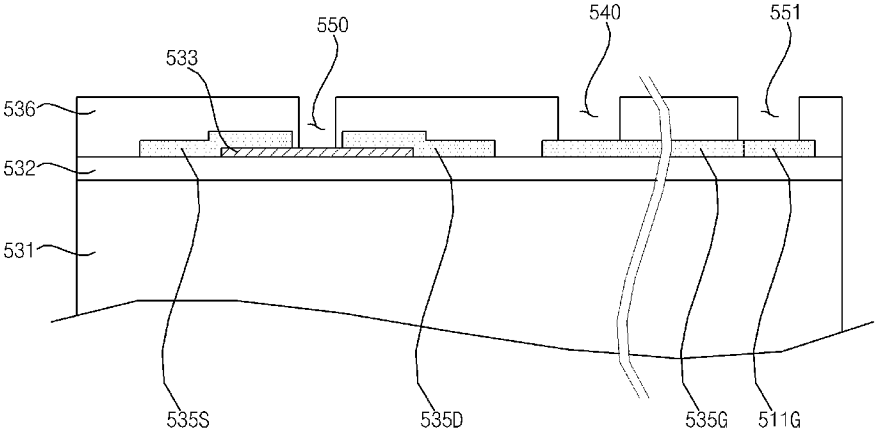
FIG. 15 is a cross-sectional view of the sensor chip taken along line V-V' of FIG. 14.
Figure 16A:
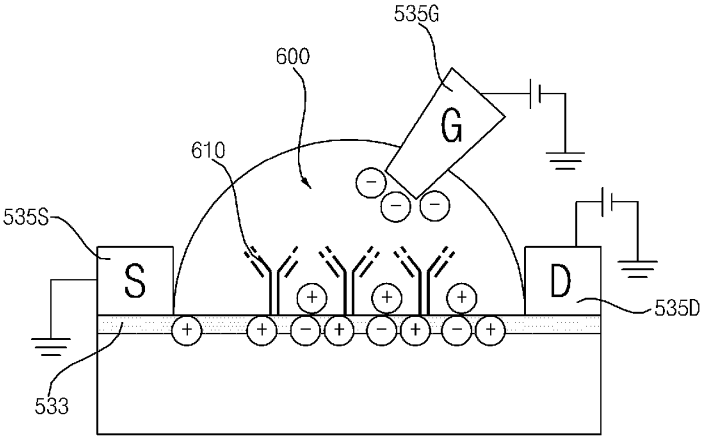
FIGS. 16A and 16B are schematic diagrams illustrating a reaction of the sensor chip of FIG. 14 according to a target material.
Figure 16B:
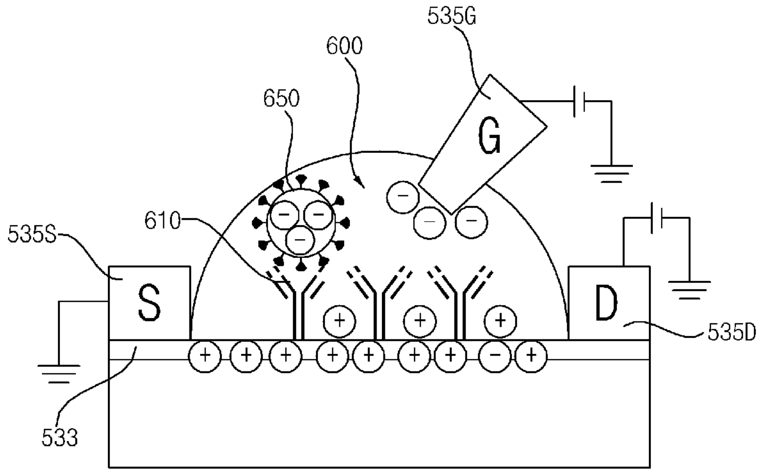
Figure 17:
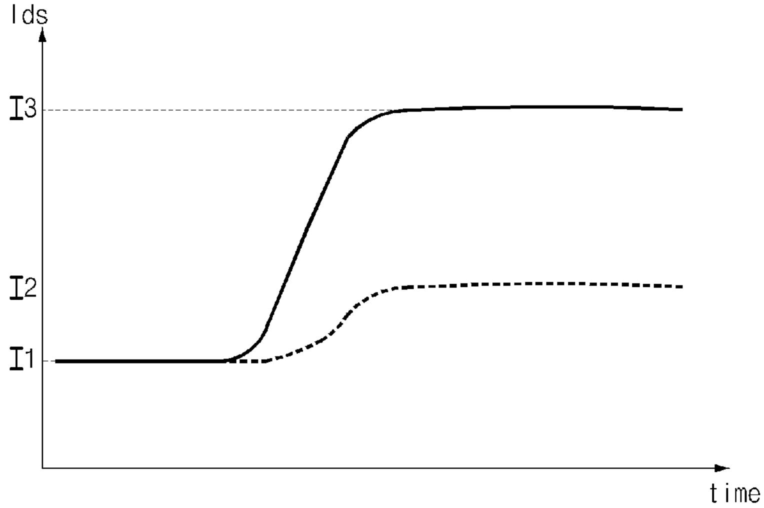
FIG. 17 is a graph illustrating a change in output current of the sensor chip according to FIGS. 16A and 16B.

FIG. 14 is a top view of one example of a sensor chip 500 applicable to FIGS. 6 and 12, FIG. 15 is a cross-sectional view of the sensor chip 500 of FIG. 14 taken along line V-V', FIGS. 16A and 16B are schematic diagrams illustrating a reaction of the sensor chip 500 of FIG. 14 according to a target material, and FIG. 17 is a graph illustrating a change in output current of the sensor chip 500 according to FIGS. 16A and 16B.

The biosensor chip 500 detects a target material from a specimen introduced into the inside by the accommodating portion 119 of the biosensor cartridge 100, and transmits an electrical signal generated by reacting with the detected target material to the pad 158 of the circuit board 150 through the electrode pad 511.

For example, the specimen can refer to saliva, a body fluid including sweat, blood, a solution diluted with serum or plasma, and the like, as a biological material.

The biosensor chip 500 is a semiconductor-based sensor chip 500 and can be manufactured as a biosensor chip 500 to which graphene is applied.

The sensor chip 500 can have various sizes depending on the type of target material, the number of target materials, and the size of the cartridge 100 and can be designed to have a size of, for example, 6×6 mm or 6×8 mm.

Referring to FIGS. 14 and 15, the biosensor chip 500 according to the present embodiment can have a rectangular shaped plane, have a front surface on which a sensor area 540 exposed to the outside through the accommodating portion 119 is formed, and be partitioned into a pad area 510 which is spaced apart from the sensor area 540 and connected to the pad 158*s* of the circuit board 150 through the connecting member 140 and a connection portion 530 connecting the sensor area 540 and the pad area 510.

A probe material, for example, an antigen, an antibody, and an enzyme, which detects a target material from a contacted specimen and reacts with the target material to generate an electrical signal, is attached to the sensor area 540.

When the sensor area 540 comes into contact with a specimen, it interacts with a target material included in the specimen to generate an electrical signal. Accordingly, the external diagnostic device 200 connected to the biosensor 100 can analyze an electrical signal generated from the biosensor 100 to detect the presence or concentration of the target material.

The sensor area 540 includes a transistor structure and has a structure where probe material is attached to a channel area 550 of the transistor.

Specifically, the sensor area 540 includes a plurality of circular or ring-shaped electrodes ring-shaped electrodes 535S (source electrode), 535D (drain electrode), and 535G (gate electrode) forming a concentric circle, and a plurality of channel areas 550 are formed between the plurality of electrodes 535S, 535D, and 535G, particularly, between the source electrode 535S and the drain electrode 535D.

An insulating layer 532 is formed on the semiconductor substrate 531, and the insulating layer 532 can be formed of oxide or nitride. When the semiconductor substrate 531 is a silicon substrate, the insulating layer 532 can be formed of silicon oxide or silicon nitride and can be formed by various methods. For example, a silicon oxide layer can be formed on the surface through heat treatment.

A plurality of channels 533 are formed on the insulating layer 532 to be spaced apart from each other.

A plurality of channels 533 are disposed by being spaced apart by a predetermined distance from the circle center O of the sensor area 540, and a central area is exposed to form the channel area 550.

The plurality of channels 533 are disposed by being spaced apart from each other on the circumference of an imaginary circle having a radius of a predetermined distance from the center O of the circle.

The plurality of channels 533 can be disposed to be spaced apart by the same angle; for example, as shown in FIG. 10, seven channels 533 can be formed, and each channel 533 can be spaced apart from the other at an angle of 45 degrees.

Alternatively, five channels 533 can be disposed so that each channel 533 can be spaced apart at an angle of 60 degrees. However, the channels 533 can be spaced apart by any angle.

One channel 533 can be patterned in a specific shape and can be formed by a semiconductor material but can also be formed by a graphene-based material that is highly reactive as a highly conductive material.

The channel 533 includes an area overlapping with the source electrode 535S and the drain electrode 535D and a channel area 550 exposed to the outside through the accommodating portion 119 between two overlapping areas.

The channel area 550 can have lower resistance in the channel area 550 as the channel 533 is formed in an I-shape to have a narrower width than the overlapping area as shown in FIG. 14 but is not limited to the specific case; instead, the channel area 550 can be formed in a bar type to have the same width from the overlapping area to the channel 533.

A source electrode 535S having the shape of the smallest circle can be formed at the center O of the circle of the sensor area 540. The source electrode 535S can be formed to have the smallest diameter and to overlap one end of the channel 533; the source electrode 535S simultaneously overlaps a plurality of channels 533 and applies a source voltage simultaneously to a plurality of channels 533.

A drain electrode 535D can be formed outside the channel area 550 to be spaced apart from the source electrode 535S.

The drain electrode 535D can be formed in a ring shape and is formed along the circumference of an imaginary circle that surrounds the channel area 550 and has a larger diameter than that of the channel area 550.

The drain electrode 535D can also overlap the plurality of channels 533 simultaneously to receive current from the plurality of channels 533 simultaneously.

One end of the drain electrode 535D is cut to form a passage through which the connection portion 521 of the source electrode 535D passes.

A gate electrode 535G is formed along the circumference of an imaginary circle having a larger diameter surrounding the drain electrode 535D.

The gate electrode 535G can have the largest area and occupy ½ to ⅔ of the sensor area 540. The gate electrode 535G is formed to be spaced apart from the source electrode, the gate electrodes 535S and 535D, and the channel area 550.

The gate electrode 535G also forms a passage and one end of the gate electrode 535G is disconnected so that the connection portions 521 of the grain electrode and the source electrodes 535S and 535D are connected to the pad 511. Specifically, the source electrode 535S is electrically connected to a source pad 511S, the drain electrode 535D is electrically connected to the drain pad 511D and the gate electrode 535G is connected to the gate pad 511G.

The electrodes 535S, 535D, and 535G of the sensor area 540 designed as shown in FIG. 14 are formed in the same layer.

Accordingly, the source electrode, the drain electrode, and the gate electrodes 535S, 535D, and 535G are all formed in the same layer and formed in one process.

For example, the source electrode, the drain electrode, and the gate electrode 535S, 535D, and 535G can be respectively formed by forming an electrode layer and simultaneously patterning a corresponding electrode layer.

Thus, a process step can be reduced, and a process time and cost can be reduced by simultaneously forming three electrodes 535S, 535D, and 535G that do not overlap each other.

The metal layer can be formed of at least one of Ni, Zn, Pd, Ag, Cd, Pt, Ga, In, and Au, but is not limited thereto.

A passivation layer 536 is formed on the electrodes 535S, 535D, and 535G.

The passivation layer 536 is formed on the entire sensor chip 500 to protect the sensor area 540 and the electrodes 535S, 535D, and 535G. However, the passivation layer 536 can formed on less than the entire sensor chip 500.

The passivation layer 536 can be formed of a material resistant to moisture and can be formed of, for example, an oxide layer, a nitride layer, or a carbide layer.

In addition, the passivation layer 536 can be applied with a polymer resin but is not limited thereto.

The passivation layer 536 exposes only the upper portion 551 of the plurality of channel areas 550, the gate electrode 540, and the plurality of pads 511 in the sensor chip 500; and covers all other areas.

Accordingly, the area exposed by the passivation layer 536 is very limited.

In particular, in the sensor area 540, only the gate electrode 535G and the channel area 550 are exposed to induce a reaction by directly contacting the specimen.

In the pad area 510, each pad 511 is exposed in an insulated state, and electrically in contact with each pad 158 of the circuit board 150 through a connecting member through an upper connecting member 140.

As shown in FIG. 16A, probe material 610 is attached to each of the channel areas 550 exposed as described above to activate the sensor.

The probe material 610 is a material that reacts specifically to a target material to be detected by the sensor. When the target material is an antigen, an antibody can be attached thereto, or when the target material is an antibody, an antigen can be attached thereto.

When the channel 533 is formed of graphene, a linker material (not shown) can be attached for smooth connection between the probe material 610 and graphene, and a process of attaching the probe material 610 after attaching a linker material on graphene is defined as an activation process.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphthalate, polycarbonate, and combinations thereof.

In addition, the linker material can be formed of a combination of polyurethane and NOA (e.g. NOA 68). However, the linker material is not limited thereto, and can be made of various polymers having flexibility.

An electrical detection signal according to a reaction of the sensor chip 500 can be described with reference to FIGS. 16A and 16B.

When the target material does not exist in the specimen as shown in FIG. 16A, the source electrode 535S receives a source voltage and the gate electrode 535G receives a gate voltage by the voltage applied to each pad 511.

The gate electrode 535G is exposed to the accommodating portion 119 and comes into contact with the specimen provided from the outside to apply a bias voltage to the specimen. Therefore, the specimen exists in a state of being partially charged with respect to the voltage of the gate electrode 535G.

At this time, the drain current Ids read from the drain electrode 535D is as shown in FIG. 17.

That is, when there is no target material reacting with the probe material 610 in the specimen 600, the drain current Ids has a first value 11, which is defined as a reference current.

At this time, as shown in FIG. 16B, when the target material 650 exists in the specimen 600, the channel 533 is charged with a specific carrier as the target material 650 reacts with the probe material 610. For example, as shown in FIG. 16B, a depletion state in which charges are accumulated in the channel 533 can proceed.

Accordingly, as the drain current Ids read from the drain electrode 535D increases, it has a second value 12 of FIG. 17.

At this time, the amount of accumulated charge is proportional to the area of the channel 533. Thus, when the number of channel 533 is one, the drain current Ids has a second value 12. When the number of channels 533 is two or more, the drain current Ids has a third value 13 greater than the second value 12. When the number of channels 533 is three or more, the drain current Ids has a fourth value 14 greater than the third value 12. Accordingly, the value of the drain current Ids read from the drain electrode 535D is amplified.

At this time, even when one channel 533 does not operate as the plurality of channels 533 are spaced apart from each other, the existence of the target material can be recognized by causing the drain current Ids to increase or decrease in other channel 533.

As described above, the graphene channel sensor chip 500 has a multi-channel structure having a plurality of channels spaced apart from each other, thereby amplifying a drain current and compensating for a malfunctioning channel.

In such a sensor chip 500, both the gate electrode 535G and the channel area 550 can be exposed by the distal end opening of the accommodating portion 119 having a circle larger than the circumference of the gate electrode 535G.

In addition, the plurality of channel areas 550 are formed to be spaced apart at the same angle and at the same distance from the center O of the sensor area 540 opened by the accommodating portion 119 such that the specimen is uniformly contacted and formed in a shape surrounding the source and drain electrodes 535S and 535D in order to dispose the channel 533 between the source and drain electrodes 535S and 535D, thereby optimizing a structure.

FIG. 14 shows electrode connection portion 521 connected from one end of each electrode 535S, 535D, and 535G to the pad 511; since each electrode connection portion 521 is made of the same metal layer as the electrodes 535S, 535D, and 535G, the connection portions do not overlap each other. Specifically, a source electrode 535S is electrically connected to a source pad 511S, the drain electrode 535D is electrically connected to the drain pad 511D and the gate electrode 535G is connected to the gate pad 511G.

FIG. 14 illustrates a case in which the pad 511 is formed in a line on one end of the sensor chip 500, but the present disclosure is not limited to the specific case.

The design of the sensor chip 500 can be variously changed as long as the transistor in which the gate electrode 535G and the plurality of channels 533 are exposed is maintained in the accommodating portion 119.

Accordingly, the position of the pad 511 can also be variously changed. However, the positions of the connecting member 140 and the connection pad 158 of the circuit board 150 are also changed according to the change in the position of the pad 511.

Figure 18:
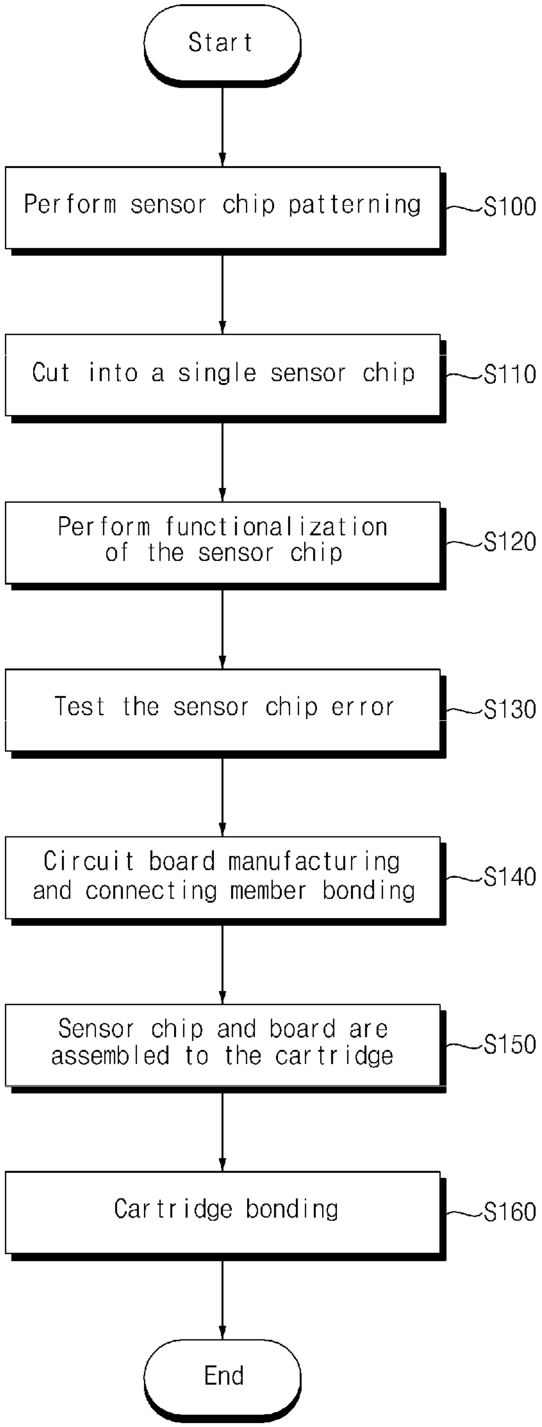
FIG. 18 is a flowchart illustrating a manufacturing process of the biosensor cartridge of FIG. 5.

The biosensor cartridge 100 accommodating the graphene-based multi-channel sensor chip 500 is manufactured through the process shown in FIG. 18.

Hereinafter, a method of manufacturing a graphene-based multi-channel sensor chip 500 according to the present disclosure will be described with reference to FIG. 18.

Referring to FIG. 18, firstly, patterning of the sensor chip 500 for manufacturing the sensor chip 500 is performed on a semiconductor wafer S100.

The manufacturing of the sensor chip 500 is a process for manufacturing the sensor chip 500 of FIGS. 14 and 15, and an insulating layer 532 made of oxide or nitride is formed on the semiconductor substrate 531.

When the semiconductor substrate 31 is a silicon substrate, the insulating layer 532 can be formed of silicon oxide or silicon nitride and can be formed by various methods. For example, a silicon oxide layer can be formed on the surface through heat treatment.

A plurality of channels 533 are formed on the insulating layer 532 to be spaced apart from each other.

At this time, one semiconductor wafer is designed to simultaneously manufacture a plurality of unit sensor chips 500 and can perform channel patterning for manufacturing the plurality of unit sensor chips 500.

A channel layer is patterned with a plurality of channels 550 designed for each unit sensor chip 500.

For example, when the plurality of channels 550 are formed of graphene, the graphene is stacked on the insulating layer and then patterned to form a plurality of channels 550 spaced apart from each other in the area of the unit sensor chip 500.

Next, at least one metal layer among Ni, Zn, Pd, Ag, Cd, Pt, Ga, In, and Au for forming the electrode 535S, 535D, 535G as shown in FIG. 14 is stacked, and the metal layer is patterned to simultaneously form the source electrode, the drain electrode, and the gate electrode 535S, 535D, 535G, the pad 511 connected to each electrode, and the connection portion 521 for connecting them. The passivation layer 536 is formed on the electrode 535S, 535D, and 535G, and patterning is performed to expose only the plurality of channel areas 550, the gate electrode 540, and the plurality of pads 511.

When a plurality of unit sensor chips 500 are generated on one semiconductor wafer as described above, a cutting process of cutting the plurality of unit sensor chips 500 into a single sensor chip 500 is performed S110.

The cutting process can be performed by laser scribing, and laser scribing can be performed together with a physical cutting process.

A single sensor chip 500 cut into a unit sensor chip 500 is defined as the sensor chip 500 of FIG. 14, and functionalization of the sensor chip 500 is performed S120.

The functionalization of the sensor chip 500 is defined as a process of attaching probe material that performs a specific reaction to a target material to be detected by each sensor to an exposed channel area of each sensor chip 500.

For the functionalization of the sensor chip 500, when the channel 533 is formed of graphene, a linker material can be attached for a smooth connection between the probe material 610 and graphene, and a process of attaching the probe material 610 after attaching the linker material on the graphene is performed.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives (NOA), epoxy, polyethylene terephthalate, polymethyl methacrylate, polyimide, polystyrene, polyethylene naphthalate, polycarbonate, and combinations thereof.

In addition, the linker material can be formed of a combination of polyurethane and NOA (e.g., NOA 68). However, the linker material is not limited thereto, and can be made of various polymers having flexibility.

When the functionalization of the sensor chip 500 is completed, a test process of the sensor chip 500 is performed S130.

In the test of the sensor chip 500, the sensor chip 500 is injected into a test equipment, and the test equipment is connected to the exposed pad(s) 511, so that the alignment and electrical signals of the pad(s) 511 are read to measure resistance.

Thus, a physical test on whether patterning is performed accurately according to a design and a functional test on whether electrical connection is performed can be simultaneously performed.

In addition, the basic resistance value of each sensor chip 500 is received, and a failure can be determined according to whether the corresponding basic resistance value is within a certain range.

When such an error check is finished, a defective sensor chip is classified and only the sensor chip 500 that passes the check can be used as a valid chip.

Meanwhile, the circuit board 150 can be manufactured through a separate process. As described above, the circuit board 150 is fabricated by cutting and punching a base member, which is the base material of the circuit board 150, according to the design of the circuit board 150, forming a circuit pattern in one side of the base member, and attaching a reinforcing plate 159 on the other side of the circuit board 150.

In this case, one side of the circuit board 150 is disposed as a rear surface, and the connection pad 158, which is a part of the circuit pattern, is exposed on the rear surface.

The connecting members 140 are respectively attached to the exposed connection pad 158 according to a preset number S140.

The bonding of the pad 158 and a first surface of the connecting member 140 can be performed by soldering so as to simultaneously satisfy the electrical and physical attachment.

Accordingly, a second surface of the connecting member 140 is maintained as a free end.

Next, in a state in which the sensor chip 500 is disposed in the area of the sensor chip 500 of the lower housing 120 of the cartridge 100 and the circuit board 150 is placed thereon, the upper housing 110 is pressed, so that the second surface of the connecting member 140 is fixed in a state of being bonded to the pad 511 of the sensor chip 500 S150.

Accordingly, electrical connection and physical connection between the circuit board 150 and the sensor chip 500 are simultaneously achieved.

In this state, the ends of the side surfaces of the lower housing 120 and the upper housing 110 of the cartridge 100 are ultrasonically fused to induce the melting of some resin and harden the melted resin to integrate the cartridge 100 S160. The manufacturing is completed in such a way that the physical separation of the upper housing 110 and the lower housing 120 is made impossible by the fusion.

Through such a manufacturing process, failure of the sensor chip 500 is firstly filtered and then assembling is performed. In the assembling step, a high-temperature process by wire bonding is not applied, so that the functionalized sensor chip 500 is prevented from being deteriorated due to heat.

In addition, since a process for protecting a device by performing plastic molding is not added after wire bonding of the sensor chip 500, deterioration of the probe material of the sensor chip 500 due to high temperature is prevented.

Figure 19:
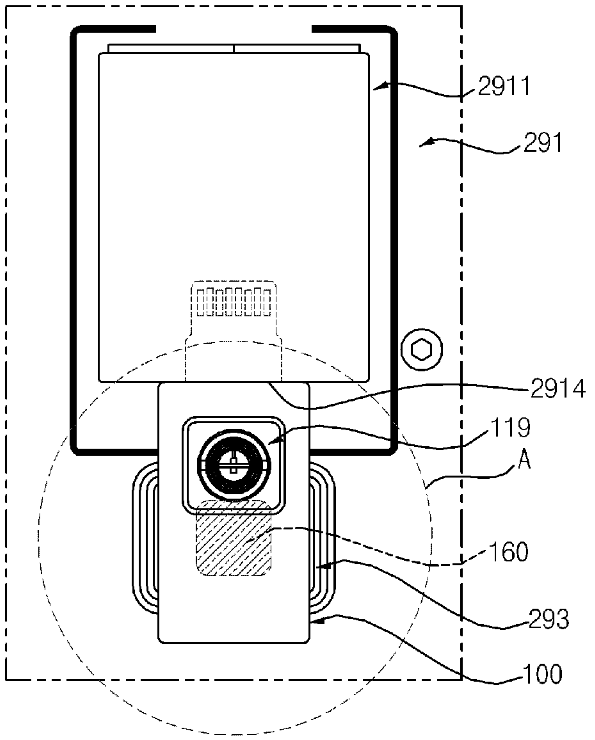
FIG. 19 is a coupling diagram in which the biosensor cartridge is coupled to the biosensor diagnostic device in the biosensor system of FIG. 1.

The biosensor cartridge 100 accommodating the graphene-based multi-channel sensor chip 500 manufactured as described above performs the certification of the sensor cartridge 100 and the diagnosis of the specimen by inserting the connection terminal 153 of the cartridge into the insertion hole 2914 of the insertion module 2911 of the diagnostic device of FIG. 2 as shown in FIG. 19.

FIG. 19 is a coupling diagram in which the biosensor cartridge 100 is coupled to the biosensor diagnostic device 200 in the biosensor system of FIG. 1.

As shown in FIG. 19, when a test target specimen (e.g., analysis specimen) is received in the accommodating portion 119 of the biosensor cartridge 100 in the biosensor system according to the present embodiment, the connection terminal 153 of the biosensor cartridge 100 is inserted into the insertion hole 2914 of the cartridge insertion module 2911 of the biosensor diagnostic device 200.

As described above, the specimen can be a body fluid, such as saliva or sweat, or blood.

When a plurality of insertion holes 2914 are disposed, the connection terminal 153 is inserted into the insertion hole 2914 of a type matching the type of the connection terminal 153.

The insertion of the cartridge connection terminal 153 can be performed in the same manner as the insertion of the USB memory as the cartridge connection terminal 153 is similar to the USB terminal.

As described above, when the biosensor cartridge 100 and the biosensor diagnostic device 200 are coupled for analysis, the state shown in FIG. 19 is maintained.

That is, the accommodating portion 119 in which the test targeting specimen is accommodated is located outside the diagnostic device 200 and transmits an electrical signal in a state in which only the connection terminal 153 is inserted into the diagnostic device 200 through the insertion hole 2914.

The rear surface 129 of the lower housing 120 of the cartridge 100 faces the front panel 291, the QR label 124 attached to the rear surface 129 of the lower housing 120 is aligned with the QR opening 293 of the front panel 291, and the QR reading module 271 is turned on so that a camera of the diagnostic device reads the QR code of the QR label 124 of the rear surface 129 of the cartridge 100 on the QR opening 293.

The operator 250 decodes the QR information to extract sensor information stored as QR information. In this case, the sensor information can include the sensor chip 500 type, linker information, probe material information, product ID, board ID, manufacturer information, manufacturing date, assembly date, test date, manufacturing number, and the like.

The operator 250 can perform a certification of the biosensor cartridge 100 by at least one cloud server 400 connectable through the wireless communication module 261.

When the biosensor cartridge 100 is genuine, the correction data is downloaded from the cloud server 400, the cartridge insertion module 2911 is driven to read the detection signal of the cartridge connection terminal 153 from the sensor controller 240, the signal conversion amplifier 210, and the signal filter 220.

At this time, the gate voltage and the source voltage are transmitted to the biosensor cartridge 100 through the sensor controller 260, and the drain current that is changed accordingly is read from the signal conversion amplifier 210.

Such read drain current value is amplified, and digitized after noise is removed, and transmitted to the operator 250.

A detection signal is decoded by executing a stored algorithm with respect to the drain current value which is the transmitted digitized detection signal, thereby reading whether the target material exists in the specimen currently accommodated in the cartridge 100.

At this time, the operator 250 downloads the correction data for a corresponding cartridge from the cloud server 400 after genuine product certification, and accordingly upgrades a corresponding algorithm, so that the optimized algorithm for the accumulated results of the same type of cartridge can be applied to the analysis.

The operator 250 reads the detection signal by performing the upgraded algorithm and transmits the result to the display module 295 for visualization.

In addition, it can operate to transmit a corresponding reading result to the cloud server 400, and transmit to a connected user terminal 300, so that a user can be notified by a designated user terminal 300.

The biosensor is not easy to determine whether it is an imitation. Even if it is genuine, sensor errors are often found from test data accumulated after manufacturing and sales. Therefore, a process of classifying the biosensor cartridge 100 in which an error has occurred is required before the test proceeds.

The biosensor system of the present embodiment can check an error including a current risk to a corresponding type of the biosensor cartridge 100 through such a certification procedure.

In addition, as the insertion of cartridge 100 and the genuine product certification are performed simultaneously, certification is performed by using a separate QR reader, and then the certified cartridge is applied to the diagnostic device 200 so that two-step operation of diagnosis can be merged into one operation. Therefore, the user's convenience is increased, and the genuine product certification of cartridge and the cartridge diagnosis are performed almost simultaneously and proceeded in a state where the cartridge inserted, so that the diagnosis result of a corresponding cartridge and the information of the cartridge are not mixed and can be clearly matched.

Figure 20A:
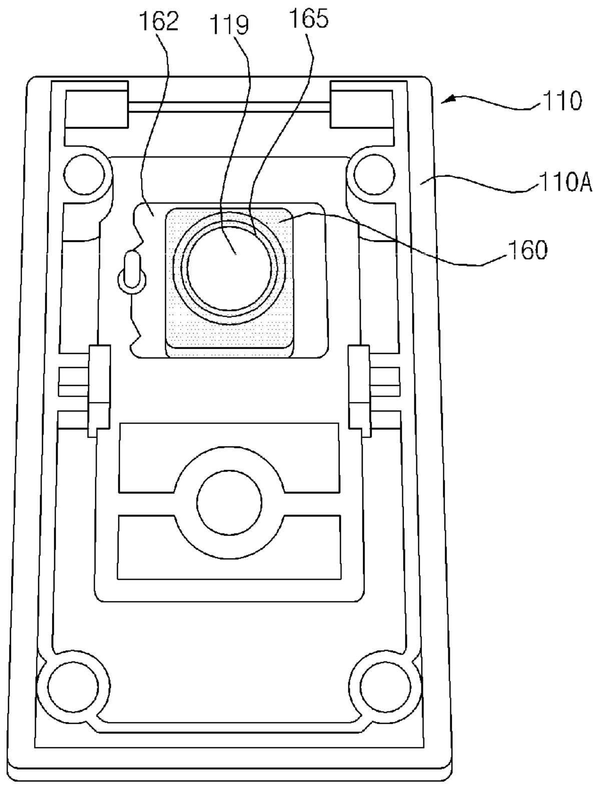
FIGS. 20A and 20B are respectively an inner top view and a cross-sectional view according to another example of the biosensor cartridge of FIG. 1.
Figure 20B:
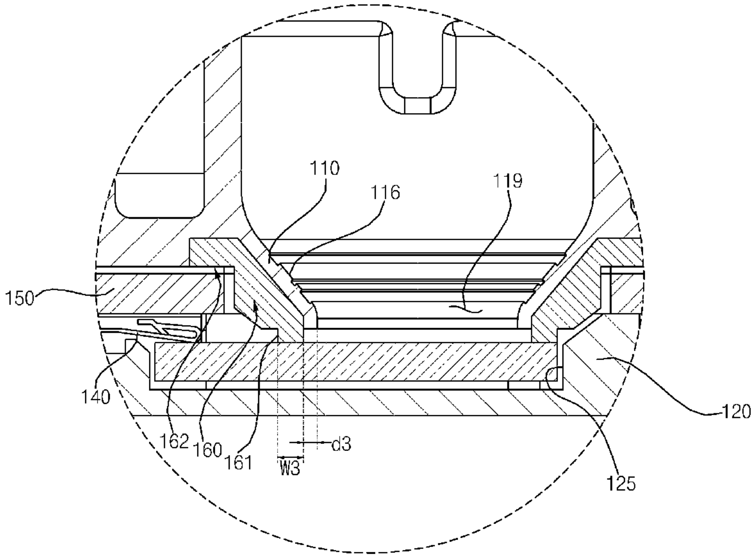

The biosensor cartridge of the biosensor system can be deformed into the shape shown in FIGS. 20A to 20B.

In what follows, a biosensor cartridge according to another embodiment of the present disclosure will be described with reference to FIGS. 20A and 20B.

FIG. 20A shows a rear view of the upper case of another example of the biosensor cartridge 100 of FIG. 1, and FIG. 20B shows a cross-sectional view of FIG. 7 to which the upper case of FIG. 20A is applied.

The configuration of the lower housing 120, the sensor chip 500, and the circuit board 150 of the biosensor cartridge 100 of FIGS. 20A and 20B is the same as that of the biosensor cartridge 100 of FIGS. 6 and 7; also, since the attachment configuration of the upper housing 110 and the lower housing 120 is the same as that of FIG. 10, a description thereof will be omitted.

Referring to FIGS. 20A and 20B, the biosensor cartridge 100 according to the present embodiment accommodates the sensor chip 500 that generates an electrical detection signal according to a target material and has a structure that includes a connection terminal 153 capable of transmitting the detection signal to an external diagnostic device 200.

At this time, on the rear surface 110A of the upper housing 110 of the biosensor cartridge 100, a molding portion 160 for bonding with and sealing the circuit board 150 and the sensor chip 500 is formed together.

The upper housing 110 faces the lower housing 120 and is coupled to the lower housing 120 and serves as an upper case capable of accommodating the circuit board 150 and the sensor chip 500 therein. In addition, an accommodating portion 119 exposing the sensor area 540 of the sensor chip 500 is formed in the upper housing 110 to accommodate a test target specimen.

The upper housing 110 is formed to have rigidity that can firmly support the connecting member 140 by pressing the connecting member 140 with a predetermined force.

When the upper housing 110 and the lower housing 120 are combined, an opening protruding the connection terminal 153 of the circuit board 150 is formed in the cross-section, and the connection terminal 153 is exposed to be inserted into the insertion hole 2914 of the external diagnostic device 200 as the connection terminal 153 of the cartridge. Due to the strong coupling between the upper housing 110 and the lower housing 120, the specimen provided to the sensor chip 500 through the accommodating portion 119 can be prevented from leaking into the housings 110 and 120. That is, if the analysis specimen leaks past the accommodating portion, it can leak onto the guard groove 113, which is shown in FIG. 10.

The accommodating portion 119 for exposing the sensor area 540 of the sensor chip 500 and accommodating a specimen is formed on the upper surface 111 of the upper housing 110. The accommodating portion 119 is a space for inducing a reaction with the exposed sensor area 540 by accommodating a test target specimen in a fluid state, e.g., in a liquid state, and the accommodating portion 119 forms a conical channel whose diameter becomes narrower as it approaches the sensor area 540 from the upper surface 111.

Therefore, the accommodating portion 119 is formed to have an inclined surface 116 such that the diameter w1 of the opening of the upper surface is larger than the diameter w2 of the opening at the end of the accommodating portion 119.

At this time, an inclination angle 81 of the inclined surface 116—the angle of the inclined surface 116 with respect to the horizontal direction (x-axis) in which the sensor chip 500 is placed, when viewed from the cross-section in FIG. 7—can be uniform but can have an inflection point.

That is, the inclination angle 81 increases as it approaches the sensor area 540, and it forms a verticality in the outermost area closest to the sensor area 540 so that it can be changed to a cylindrical passageway.

As described above, since the accommodating portion 119 has the inclined surface 116, a concave groove having a depth equal to the height from the upper surface of the upper housing 110 to the sensor area 540 is formed; a specimen is collected in the groove to induce a reaction with the probe material in the sensor area 540.

The rear surface 110A of the upper housing 110 can include an inclined portion to form the inclined surface 116 of the accommodating portion 119, as shown in FIG. 20B.

At this time, the rear surface 110A of the upper housing 110 of FIGS. 20A and 20B further includes a molding portion 160 formed along the inclined portion.

The molding portion 160 replaces the sealing part of FIG. 7.

That is, the biosensor cartridge 100 of FIGS. 20A and 20B forms the molding portion 160 sealing between the connection portion 530 of the sensor chip 500 and the upper housing 110 in the rear surface 110A of the upper housing 110.

The molding portion 160 is not formed as a separate element but is integrated with the rear surface 110A of the upper housing 110 through secondary injection during molding of the upper housing 110, and the molding portion 160 is formed and simultaneously hardened.

The upper housing 110 and the lower housing 120 can be made of at least one of polymethyl methacrylate, polycarbonate, cyclic olefine copolymer, polyethylene sulfone, and polystyrene or a material obtained by a combination of at least two or more of the above. However, the material for the housing 110, 120 is not necessarily limited to the specific example above and can be made of a polydimethylsiloxane material, which is a silicone-based organic polymer.

For example, during the first injection of the upper housing 110, polycarbonate, a polymer containing a predetermined amount of a glass fillet in the polycarbonate, or polycarbonate and acrylonitrile butadiene styrene (ABS) copolymer is injected into the mold. At this time, at a second stage, liquid silicone is injected to be formed along the rear surface 110A of the upper housing 110, specifically along the inclined portion, and to protrude by being extended below the lower opening of the inclined surface 116 to protrude.

As described above, by sequentially injecting different materials into the mold, it is possible to manufacture the upper housing 110 and the molding portion 160 in an integrated manner.

In this case, since the liquid silicone exists as liquid at room temperature and does not affect the temperature of the upper housing 110, which is a first injection, its shape can be maintained; since the liquid silicone has predetermined elasticity with a hardness of 40 (Shore), material and process costs can be reduced compared to implementing a separate sealing member.

On the other hand, the molding portion 160 formed by the hardening of the liquid silicone is aligned with the lower opening of the inclined surface 116 as shown in FIGS. 20A and 20B and includes a molding opening exposing the sensor area 540 to the lower opening.

That is, the molding portion 160 can have a molding opening 165 having a diameter w3 larger than the diameter w2 of the rear opening of the accommodating portion 119, and the rear opening and the sealing opening 131 can be arranged to have concentric circles. Accordingly, as shown in FIG. 20B, the molding portion 160 is disposed outside the lower opening of the accommodating portion 119 to form a concave groove at the end 161 in contact with the sensor area 540.

The structure above is intended to provide a tolerance when the molding unit 160 is compressed and thus avoid the risk of covering the sensor area 540 in contact with a specimen when the molding unit 160 having elasticity is pushed into the sensor area 540 due to compression of the molding portion 160.

As described above, it is possible to ensure the sealing of the specimen while securing the area of the sensor area 540 by adjusting the size of the molding opening 165 of the molding portion 160 and the opening size of the accommodating portion 119.

In addition, when being fitted so that the opening 115 of the circuit board 150 surrounds the rear surface of the inclined surface 116 of the accommodating portion 119, the molding portion 160 is formed to have a step 162 vertically in the area where the molding portion 160 meets the opening 115 of the circuit board 150.

That is, the molding portion 160 located on the rear surface of the inclined surface 116 of the accommodating portion 119 can form a step 162 corresponding to the cross-section of the opening 155 of the circuit board 150 for being fitted and coupled with the opening 155 of the circuit board 150 at the portion to which the opening 155 of the circuit board 150 is coupled.

The step 162 can have a separation distance from the side surface of the opening 155 of the circuit board 150, but is not limited thereto, and can be fitted and coupled.

It is easy to fix the circuit board 150 when being fitted and coupled without a separation distance, but a separation distance can be formed for tolerance. At this time, it is required that the width of the separation distance range from 0.05 mm to 0.2 mm.

In addition, when the rear surface of the circuit board 150 is placed in the lower housing 120, a separation distance for tolerance can be ensured from the rear surface of the upper housing 120.

As described above, since the front surface of the circuit board 150 and the molding portion 160 formed in the rear surface of the upper housing 110 are coupled with a predetermined tolerance distance, it is possible to prevent a distortion of the circuit board 150 and compensate for a process error, thereby reducing the defect rate.

As described above, since the molding portion 160 is coupled to the circuit board through the step 162 and is injected together with the upper housing 110 to contact the sensor area 540, alignment is made simple when the cartridge 100 is assembled, and the manufacturing process is simplified.

Various embodiments described herein may be implemented in a computer-readable medium using, for example, software, hardware, or some combination thereof. For example, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller. For Example, the controller is a hardware-embedded processor executing the appropriate algorithms (e.g., flowcharts) for performing the described functions and thus has sufficient structure. Also, the embodiments such as procedures and functions may be implemented together with separate software modules each of which performs at least one of functions and operations. The software codes can be implemented with a software application written in any suitable programming language. Also, the software codes can be stored in the memory and executed by the controller, thus making the controller a type of special purpose controller specifically configured to carry out the described functions and algorithms. Thus, the components shown in the drawings have sufficient structure to implement the appropriate algorithms for performing the described functions.

For a software implementation, the embodiments such as procedures and functions may be implemented together with separate software modules each of which performs at least one of functions and operations. The software codes can be implemented with a software application written in any suitable programming language. Also, the software codes may be stored in the memory and executed by the controller. Thus, the components shown in the drawings have sufficient structure to implement the appropriate algorithms for performing the described functions.

The present invention encompasses various modifications to each of the examples and embodiments discussed herein. According to the invention, one or more features described above in one embodiment or example can be equally applied to another embodiment or example described above. The features of one or more embodiments or examples described above can be combined into each of the embodiments or examples described above. Any full or partial combination of one or more embodiment or examples of the invention is also part of the invention.

What is claimed is:

1. A biosensor cartridge comprising:

a circuit board including a connection terminal configured to be electrically connectable to an external diagnostic device and a plurality of connection pads electrically connected to the connection terminal;

a sensor chip including a reactant, a plurality of electrodes, and a plurality of electrode pads electrically connected to the plurality of electrodes, the sensor chip being configured to:

detect a target material from an applied analysis specimen, and transmit an electrical signal generated by reacting with the detected target material to the connection terminal of the circuit board;

a plurality of connecting members electrically connecting the plurality of connection pads and the plurality of electrode pads; and a housing including a lower housing and an upper housing facing the lower housing and forming a space accommodating the circuit board and the sensor chip, the housing including an accommodating portion configured to accommodate the applied analysis specimen and expose the sensor chip to the applied analysis specimen, wherein the connection terminal is exposed outside the housing, wherein each of the plurality of connection members comprises:

a first surface in contact with one of the plurality of connection pads;

a second surface in contact with one of the plurality of electrode pads; and a bending portion extending between the first surface and the second surface and formed to be bent, and wherein the bending portion is elastically deformed by a pressure applied due to coupling of the upper housing and the lower housing.

2. The biosensor cartridge of claim 1, wherein the connection terminal protrudes from one side surface of the housing, and wherein the connection terminal includes at least three pins disposed in parallel on the circuit board and separated from each other.

3. The biosensor cartridge of claim 2, wherein the sensor chip further includes a pad area comprising the plurality of electrode pads and configured to transmit the electrical signal from a sensor area to the circuit board, and wherein the sensor area includes:

a board;

a channel area formed on the board and including at least one channel;

the plurality of electrodes including:

a source electrode;

a drain electrode spaced apart from the source electrode by the at least one channel; and a gate electrode spaced apart from the source electrode and the drain electrode and configured to apply a bias voltage to the applied analysis specimen; and a passivation layer covering the sensor chip and open only an upper portion of the channel area and the gate electrode.

4. The biosensor cartridge of claim 3, wherein the plurality of electrode pads include:

a source pad connected to the source electrode;

a drain pad connected to the drain electrode; and a gate pad connected to the gate electrode, wherein the source pad, the drain pad and the gate pad are formed in the pad area of the sensor chip, and wherein the circuit board further includes:

a board opening that opens the sensor area of the sensor chip, and wherein the plurality of connection pads are formed around the board opening, each of the plurality of connection pads overlapping a respective one of the source pad, the drain pad and the gate pad.

5. The biosensor cartridge of claim 4, wherein each of the plurality of connection pads is connected one-to-one to each of the source pad, the drain pad, and the gate pad of the sensor chip, and wherein each of the plurality of connecting members electrically connects a corresponding one of the plurality of connection pads of the circuit board to a corresponding one of the source pad, the drain pad, or the gate pad of the sensor chip.

6. The biosensor cartridge of claim 5, wherein the sensor chip is disposed on an inner surface of the lower housing, and the circuit board is disposed on the sensor chip so that the sensor area of the sensor chip is opened and the pad area of the sensor chip comes into contact with the plurality of connection pads of the circuit board, and wherein the plurality of connecting members are attached between the pad area of the sensor chip and the plurality of connection pads of the circuit board.

7. The biosensor cartridge of claim 6, wherein the upper housing and the lower housing are fused and integrated and accommodate the sensor chip and the circuit board.

8. The biosensor cartridge of claim 1, wherein the circuit board further includes:

a first surface on which the connection terminal is formed; and a reinforcing member that entirely covers a second surface of the circuit board, the second surface of the circuit board being opposite to the first surface.

9. The biosensor cartridge of claim 4, wherein the housing includes an upper surface, wherein the accommodating portion of the housing is recessed from the upper surface of the housing, has an inclined surface, has a diameter that gradually decreases away from the upper surface, and accommodates the applied analysis specimen for being introduced into the sensor area of the sensor chip, and wherein the biosensor cartridge further includes a sealing part sealing between an end of the inclined surface and the sensor area.

10. The biosensor cartridge of claim 9, wherein the sealing part includes a sealing opening having a larger diameter than a diameter of the end of the inclined surface, and wherein the sealing opening is aligned with the accommodating portion and the sensor chip so that the sealing opening exposes the sensor area.

11. The biosensor cartridge of claim 9, wherein the inclined surface of the accommodating portion includes a step portion coupled to an end surface of the board opening in an area in contact with the board opening of the circuit board.

12. The biosensor cartridge of claim 11, wherein the housing includes a lower housing, and an upper housing facing the lower housing and forming a space accommodating the sensor chip and the circuit board, and wherein the sealing part is formed of a material different from that of the upper housing and is sequentially molded, injected, and cured to be integrated with the upper housing.

13. The biosensor cartridge of claim 12, wherein the upper housing is formed by injecting a resin into a mold, and wherein the sealing part is formed by injecting silicone on the inclined surface of the accommodation portion.

14. The biosensor cartridge of claim 9, wherein the accommodating portion further includes a guide wall protruding upwards from the upper surface of the housing and accommodating the applied analysis specimen.

15. The biosensor cartridge of claim 14, wherein the accommodating portion further includes a guide groove that is recessed to surround the guide wall on the upper surface of the housing and accommodates the applied analysis specimen flowing from the guide wall.

* * * * *